United States Patent
Suk et al.

(10) Patent No.: US 9,675,711 B2
(45) Date of Patent: *Jun. 13, 2017

(54) MUCUS PENETRATING GENE CARRIERS

(71) Applicant: The Johns Hopkins University, Baltimore, MD (US)

(72) Inventors: Jung Soo Suk, Baltimore, MD (US); Justin Scot Hanes, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/144,077

(22) Filed: May 2, 2016

(65) Prior Publication Data

US 2016/0243257 A1    Aug. 25, 2016

Related U.S. Application Data

(63) Continuation of application No. 13/984,386, filed as application No. PCT/US2012/024344 on Feb. 8, 2012, now Pat. No. 9,327,037.

(60) Provisional application No. 61/440,647, filed on Feb. 8, 2011.

(51) Int. Cl.
    *A61K 48/00*    (2006.01)
    *A61K 47/48*    (2006.01)
    *C12N 15/87*    (2006.01)

(52) U.S. Cl.
    CPC .... *A61K 48/0041* (2013.01); *A61K 47/48192* (2013.01); *A61K 47/48215* (2013.01); *A61K 48/0075* (2013.01); *C12N 15/87* (2013.01)

(58) Field of Classification Search
    CPC ........ A61K 47/48192; A61K 47/48215; A61K 48/0041; C12N 15/87
    USPC ........ 424/497, 94.6, 490; 435/325, 375, 455
    See application file for complete search history.

(56) References Cited

U.S. PATENT DOCUMENTS

| | | |
|---|---|---|
| 4,027,676 A | 6/1977 | Mattei |
| 4,201,216 A | 5/1980 | Mattei |
| 4,857,602 A | 8/1989 | Casey |
| 4,994,074 A | 2/1991 | Bezwada |
| 4,997,652 A | 3/1991 | Wong |
| 5,034,506 A | 7/1991 | Summerton |
| 5,412,072 A | 5/1995 | Sakurai |
| 5,522,842 A | 6/1996 | Shalaby |
| 5,552,160 A | 9/1996 | Liversidge |
| 5,578,325 A | 11/1996 | Domb |
| 5,710,135 A | 1/1998 | Leenders |
| 5,869,130 A | 2/1999 | Ferrier |
| 5,932,462 A | 8/1999 | Harris |
| 6,007,845 A | 12/1999 | Domb |
| 6,235,869 B1 | 5/2001 | Roby |
| 6,287,588 B1 | 9/2001 | Shih |
| 6,413,539 B1 | 7/2002 | Shalaby |
| 6,495,164 B1 | 12/2002 | Ramstack |
| 6,589,549 B2 | 7/2003 | Shih |
| 6,706,289 B2 | 3/2004 | Lewis |
| 7,550,154 B2 | 6/2009 | Saltzman |
| 7,638,137 B2 | 12/2009 | Chauhan |
| 7,645,736 B2 | 1/2010 | Bender |
| 7,648,959 B2 | 1/2010 | Bender |
| 8,071,795 B2 | 12/2011 | VanMeir |
| 8,354,476 B2 | 1/2013 | Hanes |
| 8,394,799 B2 | 3/2013 | Lee |
| 8,409,607 B2 | 4/2013 | Hughes |
| 8,465,778 B2 | 6/2013 | Hughes |
| 8,481,069 B2 | 7/2013 | Hughes |
| 8,512,738 B2 | 8/2013 | Edelman |
| 8,628,801 B2 | 1/2014 | Garreta |
| 8,632,809 B2 | 1/2014 | Asgharian |
| 8,663,674 B2 | 3/2014 | Wen |
| 8,911,768 B2 | 12/2014 | Whitcup |
| 9,327,037 B2 * | 5/2016 | Suk ............... A61K 48/0041 |

(Continued)

FOREIGN PATENT DOCUMENTS

| | | |
|---|---|---|
| WO | 9207866 | 5/1992 |
| WO | 9859064 | 12/1998 |

(Continued)

OTHER PUBLICATIONS

Erdmann and Uhrich, "Synthesis and degradation characteristics of salicyclic acid-derived poly(anhydride-esters)", Biomaterials, 21:1941-6 (2000).
Grisanti and Ziemssen, "Bevacizumab: Off-label uses in ophthalmology", Indian J Ophthalmol., 55(6):417-20 (2007).
Sagong, et al., "Intravitreal becacizumab for the treatment of neovascular glaucoma associated with central retinal artery occlusion", Koren J Ophthalmol., 23:215-8 (2009).
Aich, et al., "Developmnt of delivery methods for carbohyfrate-based drugs; controlled release of biologically-active shott chain fatty acid-hexosamine analogs", Glycoconj. J., 27 (4):445-59 (2010).
Apgar, et al., "Multiple-particle tracking measurements of heterogeneities in solutions of actin filaments and actin bundles", Biophys. J., 79:1095-1106 (2000).

(Continued)

*Primary Examiner* — Janet Epps-Smith
(74) *Attorney, Agent, or Firm* — PABST PATENT GROUP LLP

(57) ABSTRACT

Nanoparticles gene carriers, particularly nanoparticle gene carriers which exhibit increased rates of diffusion through cystic fibrosis (CF) mucus, as well as methods of making and using thereof, are described herein. The nanoparticle gene carriers are formed from a nucleic acid complexed to one or more biocompatible, polycationic polymers. The nanoparticle gene carriers also contain one or more mucus resistant polymers. In a particularly preferred embodiment, the nanoparticle gene carrier is a nanoparticle formed from one or more nucleic acids, PEI, and a mucus-resistant/diffusive graft copolymer composed of a PEI backbone functionalized by one or more PEG side chains. The nanoparticle gene carriers can efficiently diffuse through CF mucus, and can effectively serve as a vehicle to administer one or more nucleic acids to a patient suffering from CF.

13 Claims, 7 Drawing Sheets

(56) References Cited

U.S. PATENT DOCUMENTS

| | | |
|---|---|---|
| 2003/0042137 A1 | 3/2003 | Mao |
| 2003/0118550 A1 | 6/2003 | Kabanov |
| 2004/0162580 A1 | 8/2004 | Hain |
| 2004/0209806 A1 | 10/2004 | Rothenberg |
| 2004/0209807 A1 | 10/2004 | Quay |
| 2004/0234611 A1 | 11/2004 | Ahlheim |
| 2004/0258763 A1 | 12/2004 | Bell |
| 2005/0009910 A1 | 1/2005 | Hughes |
| 2005/0070448 A1 | 3/2005 | Kupper |
| 2005/0149118 A1 | 7/2005 | Koyfman |
| 2005/0149119 A1 | 7/2005 | Koyfman |
| 2007/0071756 A1 | 3/2007 | Peyman |
| 2007/0087989 A1 | 4/2007 | Huang |
| 2007/0111959 A1 | 5/2007 | Yockman |
| 2007/0149593 A1 | 6/2007 | Ghosh |
| 2007/0231360 A1 | 10/2007 | Peyman |
| 2007/0238654 A1 | 10/2007 | Deschatelets |
| 2008/0086199 A1 | 4/2008 | Dave |
| 2008/0166411 A1 | 7/2008 | Shah |
| 2008/0166414 A1 | 7/2008 | Hanes |
| 2008/0268243 A1 | 10/2008 | Stopek |
| 2008/0287341 A1 | 11/2008 | Chen |
| 2008/0287990 A1 | 11/2008 | Smit |
| 2008/0305172 A1 | 12/2008 | Ahlheim |
| 2009/0011040 A1 | 1/2009 | Naash |
| 2009/0060979 A1 | 3/2009 | Bezwada |
| 2009/0087494 A1 | 4/2009 | Kompella |
| 2009/0138041 A1 | 5/2009 | Stopek |
| 2009/0203709 A1 | 8/2009 | Steinberg |
| 2009/0220572 A1 | 9/2009 | Deschatelets |
| 2009/0226531 A1 | 9/2009 | Lyons |
| 2009/0234375 A1 | 9/2009 | Simon |
| 2009/0291919 A1 | 11/2009 | Kaushal |
| 2010/0034749 A1 | 2/2010 | Schulze |
| 2010/0094340 A1 | 4/2010 | Stopek |
| 2010/0152831 A1 | 6/2010 | Guo |
| 2010/0209469 A1 | 8/2010 | Bezwada |
| 2010/0227905 A1 | 9/2010 | Kabra |
| 2011/0264139 A1 | 10/2011 | Hunter |
| 2012/0041481 A1 | 2/2012 | Daniloff |
| 2012/0052041 A1 | 3/2012 | Basu |
| 2012/0121661 A1 | 5/2012 | Schwartz |
| 2012/0157499 A1 | 6/2012 | Hughes |
| 2012/0201873 A1 | 8/2012 | Hohlbaum |
| 2012/0245629 A1 | 9/2012 | Gross |
| 2012/0269894 A1 | 10/2012 | Ahlheim |
| 2012/0288464 A1 | 11/2012 | Carmichael |
| 2012/0303010 A1 | 11/2012 | Vijfvinkel |
| 2013/0041407 A1 | 2/2013 | Montenegro |
| 2013/0071349 A1 | 3/2013 | Robinson |
| 2013/0122064 A1 | 5/2013 | Ahlheim |
| 2013/0226234 A1 | 8/2013 | Avelar |
| 2013/0316001 A1 | 11/2013 | Popov |
| 2013/0316006 A1 | 11/2013 | Popov |
| 2013/0316009 A1 | 11/2013 | Popov |
| 2014/0031408 A1 | 1/2014 | Edelman |
| 2014/0107025 A1 | 4/2014 | Wirostko |
| 2014/0178475 A1 | 6/2014 | Figueiredo |
| 2014/0212661 A1 | 7/2014 | Khan |
| 2014/0248358 A1 | 9/2014 | Figueiredo |
| 2014/0249158 A1 | 9/2014 | Figueiredo |
| 2014/0276482 A1 | 9/2014 | Astafieva |
| 2014/0294986 A1 | 10/2014 | Liu |

FOREIGN PATENT DOCUMENTS

| | | |
|---|---|---|
| WO | 9901498 | 1/1999 |
| WO | 0046147 | 8/2000 |
| WO | 0202432 | 3/2002 |
| WO | 0238127 | 5/2002 |
| WO | 02060412 | 8/2002 |
| WO | 2005012407 | 2/2005 |
| WO | 2005072710 | 8/2005 |
| WO | 2006063249 | 6/2006 |
| WO | 2006109177 | 10/2006 |
| WO | 2006122542 | 11/2006 |
| WO | 2007016380 | 2/2007 |
| WO | 2007084418 | 7/2007 |
| WO | 2007133812 | 11/2007 |
| WO | 2008030557 | 3/2008 |
| WO | 2009151539 | 12/2009 |
| WO | 2010040188 | 4/2010 |
| WO | 2010086406 | 8/2010 |
| WO | 2010132664 | 11/2010 |
| WO | 2013166408 | 11/2013 |
| WO | 2013166436 | 11/2013 |
| WO | 2014047439 | 3/2014 |

OTHER PUBLICATIONS

Ben-Shabat, S. et al.,PEG-PLA block copolymer as potential drug carrier: preparation and characterization. Macromol. Biosci. 6:1019-1025 (2006).

Beyerle, et al., "PEGylation affects cytotoxicity and cell-compatibility of poly(ethylene imine) tor lung application: structure-function relationships", Toxicol. Appl. Pharmacol. 242:146-54 (2010).

Blessing, et al., "Monomolecular collapse of plasmid DNA into stable virus-like particles", PNAS, 95:1427-31 (1998).

Bourges, et al., "Pcular drug delivery targeting the retina and retinal pigment epithelium using polyactide nanoparticles", Inv Ophthalmology Vis Sci., 44 (8):3562-9 (2003).

Cone, "Barier properties of mucus", Adv. Drug Deliv. Rev., 61:75-78 (2009).

Dauty, et al., "Dimerizable cationic detergents with a low cmc condense plasmid DNA into nanometric particles and transfect cells in culture", J. Am. Chem. Soc. 123:9227-34 (2001).

de Kozak, et al., "Intraocular injection of tamoxifen-loaded nanoparticles: a new treatment of experimental autoimmune uveoeretinitis", Eur. J Immunol., 34:3702-12 (2004).

Deosarkar, et al.., "Polymeric particles conjugated with a ligand to VCAM-1 exhibit selective, avid, and focal adhesion to sites of atherosclerosis", Biotech. Bioeng., 101(2):400-7 (2008).

Desai, "Pluronic F127-based ocular delivery system containing biodegradable polyisobutylcyanoacrylate nanocapsules of pilocarpine", Drug Delivery, 7:201-7 (2000).

Dong, et al., "Vascular cell-adhesion molecule-1 plays a central role in he proangiogenic effects of oxidative stress", PNAS, 108(35):14614-9 (2011).

Escobar-Chavez, "Application of thermo-reversible pluronic F-127 gels in pharmaceutical formulations", J Pharma Sci., 9(3):339-58 (2006).

Ferrari, et al., "Barriers to and new approaches for gene therapy and gene delivery in cystic fibrosis", Adv. Drug Deliv. Rev. 54:1373-93 (2002).

Ferrari, et al., "Immunological hurdles to lung gene therapy", Clin. Exp. Immunol., 132:1-8 (2003).

Ferrari, et al., "Polyethylenimine shows properties of interest for cystic fibrosis gene therapy", Biochemica Biophysica Acta., 1447(2-3):219-25 (1999).

Fiegel, et al., "Poly(ether-anhydride) dry powder aerosols for sustained drug delivery in the lungs", J Control Release, 96:411-23 (2004).

Fischer, et al., "A novel non-viral vector for DNA delivery based on low molecular weight, branched polyethylenimine: effect of molecular weight on transfection efficiency and cytotoxicity", Pharm. Res. 16:1273-9 (1999).

Flotte, et al., "Gene therapy in cystic fibrosis", Chest, 120(3 suppl) 124S-131S (2001).

Giannavola, et al., "Influence of preparation conditions on Acyclovir-loaded poly-d, l-lactic acid nanospheres and effect of PEG coating on ocular drug bioavailability", Pharma. Res., 20(4):584-90 (2003).

Gou, et al., "Synthesis, self-assembly, and drug-loading capacity of well-defined cyclodextrin-centered drug-conjugated amphiphilic A 14 B 7 miktoarm star copolymers based on poly([epsilon]-caprolactone) and Poly(ethylene glycol)", Biomacromolecules, 11(4):934-43 (2010).

(56) References Cited

OTHER PUBLICATIONS

Govender, et al., "PLGA nanoparticles prepared by nanoprecipitation: drug loading and release studies of a water soluble drug", J Cont. Rel., 57:171-85 (1999).
Gregory, et al., "Expression and characteriztion of the cystic fibrosis transmembrane conductance regulator", Nature, 347:382-6 (1990).
Griesenbach and Alton, "Gene transfer to the lung: lessons learned from more than 2 decades of CF gene therapy", Adv. Drug Deliv. Rev. 61:128-39 (2009).
Hida, et al., "Common gene therapy viral vectors do not efficiently penetrate sputum from cystic fibrosis patients", PLoS One. 6:e19919 (2011).
Iwase, et al., "Safe and effective polymeric-doxorubicin conjugate nanoparticles for prolonged antiagiogenic activity in the eye", Retrieved from the internet: URL:http://www.abstractsonline.com/Plan/ViewAbstract.aspx?.
Jiang, et al., "Efficiency of cationic lipid-mediated transfection of polarized and differentiated airway epithelial cells in vitro and in vivo", Hum. Gene. Ther. 9:1531-42 (1998).
Kichler, et al., "Intranasal gene delivery with a polyethylenimine-PEG conjugate", J. Control. Release, 81:379-8 (2002).
Kleemann, et al., "Modified polyethylenimines as non-viral gene delivery systems for aerosol gene therapy: investigations of the complex structure and stability during air-jet and ultrasonic nabulization", J Controlled Release, 100(3):437-50 (2004).
Kleemann, et al., "Nano-carriers for DNA delivery to the lung based upon a TAT-derived peptide covalently coupled to PEG-PEI", J Controlled Release, 109 (1-3):299-316 (2005).
Kompella, et al., "Luteinizing hormone-releasing hormone agonist and transferrin functionalizations enhance nanoparticle delivery in a novel bovine ex vivo eye model", Mol. Vis., 12:1185-98 (2006).
Lai, et al., "Mucus-penetrating nanoparticles for drug and gene delivery to mucosal tissues", Adv. Drug Deliv. Rev. 61:158-71 (2009).
Lai, et al., "Nanoparticles reveal that human cervicovaginal mucus is riddled with pores larger than viruses", PNAS, 107:598-603 (2010).
Lai, et al., "Rapid transport of large polymeric nanoparticles in flesh undiluted human mucus", PNAS, 104(5):1482-7 (2007).
Matsui, et al., "Loss of binding and entry of liposome-DNA complexes decreases transfection efficiency in differentiated airway epithelial cells", J. Biol. Chem. 272:1117-26 (1997).
Newman, et al., "Uptake of poly(D,L-lactic-co-glycolic acid) microspheres by antigen-presenting cells in vivo", J Biomed Mater Res., 60(3):480-6 (2002).
Ogris, et al., "PEGylated DNA/transferrin-PEI complexes: reduced interaction with blood components, extented circulation in blood and potential for systemic gene delivery", Gene Ther., 6:595-605 (1999).
Okamoto, et. al., Transgenic mice with increased expression of vascular endothelial growth factor in the retina: a new model of intraretinal and subretinal neovascularization, Am. J. Pathol. 151:281-291 (1997).
Rich, et al., "Expression of cystic fibrosis transmembrane conductance regulator corrects defective chloride channel regulation in cystic fibrosis airway epithelial cells", Nature, 347:358-62 (1990).
Riordan, et al., "Identification of the cystic fibrosis gene: cloning and characterization of complementary DNA", Science 245:1066-73 (1989).
Saishin, et al., "VEGF-TRAP(R1R2) suppresses choroidal neovascularization and VEGF-induced breakdown of the blood-retinal barrier", J. Cell Physiol., 195:241-8 (2003).
Sanders, et al., "Cystic fibrosis sputum: a barrier to the transport of nanospheres", Am. J. Respir. Crit. Care Med., 162:1905-11 (2000).
Sanders, et al., "Extracellular barriers in respiratory gene therapy", Adv. Drug Deliv. Rev. 61:115-27 (2009).
Scheule, et al., "Basis of pulmonary toxicity associated with cationic lipid-mediated gene transfer to the mammalian lung", Hum. Gene Ther., 8:689-707 (1997).
Singh, et al., "Cationic micropacticles: A potent delivery system for DNA vaccines", PNAS, 98(2):811-6 (2000).
Smith, et al., Oxygen-induced retinopathy in the mouse, Invest. Ophthalmol. Vis. Sci. 35:101-111 (1994).
Sobczak, et al., "Synthesis and characterization of polyester conjugates of ciprofloxacin", Eu. J. Med Chem., 45(9):3844-9 (2010).
Soppimath, et al., "Biodegradable polymeric nanoparticles as drug delivery device", J Cont. Release, 70:1-20 (2001).
Sterchak, et al., "Unchanged stereoregular nucleic acid analogues I Synthesis of a cytosine-containing oligomer with a carbonate internucleoside linkages", J Organic Chem., 52:4202, (1987).
Suh, et al., "Efficient active transport of gene nanocarriers to the cell nucleus", PNAS, 100:3878-82 (2003).
Suh, et al., "PEGylation nanoparticles improves their cytoplasmic transport", Int. J Nanomed., 2(4):735-41 (2007).
Suh, et al., "Real-time multiple-particle tracking: applications to drug and gene delivery", Adv. Drug Deliv. Rev. 57(1):63-78 (2005).
Suk, et al., "N-acetylcysteine enhances cystic fibrosis sputum penetration and airway gene transfer by highly compacted DNA nanoparticles", Mol. Ther. 19:1981-9 (2011a).
Suk, et al., "Overcoming the cystic fibrosis sputum barrier to nanoparticle-based gene carriers", (Ph. D. thesis) John Hospkins, Baltimore, Maryland, (Feb. 10, 2011b).
Suk, et al., "Quantifying the intracellular transport of viral and nonviral gene vectors in primary neurons", Exp. Biol. Med., 232:461-9 (2007).
Suk, et al., "The penetration of fresh undiluted sputum expectorated by cystic fibrosis patients by non-adhesive polymer nanoparticles", Biomaterials. 30:2591-7 (2009).
Tanaka, et al., "Development of cell-penetrating peptide-modified MPEG-PCL diblock copolymeric nanoparticles for systemic gene delivery", Intl J Pharmac., 396(1-2):229-38 (2010).
Tang, et al., "Biodegradable polymer nanoparticles that rapidly penetrate the human mucus barrier", PNAS, 106:19268-73 (2009).
Tang, et al., "Enhanced efficacy of local etoposide delivery by poly(ether-anhydride)particles against small cell lung cancer in vivo", Biomaterials, 31:339-44 (2010).
Tang, et al., "Polyethylene glycol modified polyethylenimine for improved CNS gene transfer: effects of PEGylation extent", Biomaterials, 24(13):2351-62 (2003).
Terry, "Tenary particles for effective vaccine delivery to the pulmonary system", (Ph.D. Thesis, UMI ProQuest, Ann Arbor (2008).
Tobe, et al., "Targeted disruption of the FGF2 gene does not prevent choroidal neovascularization in a murine model", Am. J. Pathol. 153:1641-1646 (1998).
Veronese, et al., "PEG-doxorubicin conjugates: influence of polymer structure on drug release, in vitro cytotoxicity, biodistribution, and antitumor activity", Bioconjig Chem., 16 (4):775-84 (2005).
Voynow and Rubin, "Mucins, mucus, and sputum", Chest. 135:505-12 (2009).
Yang, et al., Biodegradable nanoparticles composed entirely of safe materials that.
Yokoyama, et al., "Characterization and anticancer activity of the micelle-forming polymeric anticancer drug adriamycin-conjugated poly(ethylene glycol)-poly(aspartic acid) block copolymer", Cancer Res., 50:1693-1700 (1990).
Yoshida, et al., Digoxin inhibits retinal ischemia-induced HIF-1alpha expression and ocular neovascularization, FASEB J. 24:1759-1767 (2010).

* cited by examiner

MUCUS PENETRATING GENE CARRIERS

CROSS REFERENCE TO RELATED APPLICATIONS

This application is a continuation of U.S. Ser. No. 13/984,386, filed on Aug. 8, 2013, entitled "Mucus Penetrating Gene Carriers", by Jung Soo Suk and Justin Scot Hanes, which is a National Stage of International Application No. PCT/US2012/024344 filed with the Patent Cooperation Treaty on Feb. 8, 2012, which claims priority to and benefit of U.S. Provisional Application No. 61/440,647 entitled "Synthetic Sputum-Penetrating Gene Carriers and Methods of Use" by Jung Soo Suk and Justin Hanes, filed in the U.S. Patent and Trademark Office on Feb. 8, 2011, all of which are hereby incorporated by reference in its entirety.

STATEMENT REGARDING FEDERALLY SPONSORED RESEARCH OR DEVELOPMENT

This invention was made with Government Support under Agreements P01 HL51811 and 1 R01 EB003558 awarded to Justin Scot Hanes by the National Institutes of Health. The Government has certain rights in the invention.

FIELD OF THE INVENTION

This invention is generally in the field of gene delivery, and in particular, nanoparticle carriers with high diffusivity through mucus, including human cystic fibrosis mucus, as well as methods using these nanoparticles to deliver therapeutic agents to treat patients with a variety of diseases, including cystic fibrosis.

BACKGROUND OF THE INVENTION

Cystic fibrosis (CF) is an autosomal recessive genetic disease caused by mutations in the cystic fibrosis transmembrane regulator (CFTR) gene, which encodes for an apical membrane epithelial protein that functions as a regulator of several channels, including the c-AMP-regulated chloride channel. As a result, chloride transfer across the epithelial membranes of CF patients is abnormal.

While CF symptoms appear in a number of organ systems, including the respiratory, gastrointestinal, and reproductive tract, for most patients, the most important pathological changes associated with the CFTR defect are observed in the lungs. Patients with suffering from CF produce excessive quantities of abnormally viscous mucus, which blocks the patient's bronchi and readily becomes infected. As a result, CF patients are stricken with chronic respiratory infections, including *Pseudomonas* infections, causing inflammation, progressive airway damage, and bronchiectasis. Pulmonary complications are the primary cause of CF-related morbidity and mortality in CF patients. Although improved treatment of lung disease has increased survival in CF patients, the median predicted age for survival for CF patients is only 35 years. In addition, CF patients continue to have significant morbidity, including frequent hospitalizations.

Mutations in a single gene—the Cystic Fibrosis Transmembrane Regulator (CFTR) gene—causes CF. The gene was discovered in 1989. Since then, more than 900 mutations of this single gene have been identified. In normal cells, the CFTR protein acts as a channel that allows cells to release chloride and other ions. But in people with CF, this protein is defective and the cells do not release the chloride. The result is an improper salt balance in the cells and thick, sticky mucus. Researchers are focusing on ways to cure CF by correcting the defective gene, or correcting the defective protein. Aerosol gene therapy is the most direct therapeutic strategy for CF lung diseases. Since the discovery of the CFTR gene in 1989, a large number of gene carrier, including both viral and non-viral systems, have been developed and tested in the lungs of CF patients (Griesenbach, U. and Alton, E. W. F. W. *Adv. Drug Deliv. Rev.* 61:128-139 (2009)).

As described by Flotte, et al., in CHEST 120(3 suppl) 124S-131S (2001), cystic fibrosis transmembrane conductance regulator (CFTR) gene replacement can decrease morbidity and mortality from cystic fibrosis (CF). In vivo gene transfers have been accomplished in CF patients. Choice of vector, mode of delivery to airways, translocation of genetic information, and sufficient expression level of the normalized CFTR gene are issues that limit efficacy. Initial studies with adenovirus (Ad) vectors resulted in a vector that was efficient for gene transfer with dose-limiting inflammatory effects due to the large amount of viral protein delivered. The next generation of Ad vectors, with more viral coding sequence deletions, has a longer duration of activity and elicits a lesser degree of cell-mediated immunity in mice. A more recent generation of Ad vectors has no viral genes remaining. Despite these changes, the problem of humoral immunity remains with Ad vectors. A variety of strategies such as vector systems requiring single, or widely spaced, administrations, pharmacologic immunosuppression at administration, creation of a stealth vector, modification of immunogenic epitopes, or tolerance induction have been considered to circumvent humoral immunity. The level of CFTR messenger RNA expression is difficult to ascertain with adeno-associated virus (AAV) vectors since the small size of the vector relative to the CFTR gene leaves no space for vector-specific sequences on which to base assays to distinguish endogenous from vector-expressed messenger RNA. In general, AAV vectors appear to be safer and have superior duration profiles, but do not elimination the problems with immune responses. Another challenge to the development of clinically feasible gene therapy is delivery mode. Early pulmonary delivery systems relied on the direct instillation of aerosolized vectors, which can result in the induction of adverse reactions because vector is delivered into the lung parenchyma. More recent studies have examined the potential for using spray technologies to target aerosolized AAV vectors to the larger central airways, thereby avoiding alveolar exposure and adverse effects. Other modes of delivery, such as cationic liposomes, lipid-DNA complexes, generally have been less efficient than viral vectors but do not stimulate inflammatory and immunologic responses.

Despite many years of research efforts and investment, there has been little success with CF gene therapy to date. The failures of gene therapies for CF have been attributed to a number of biological barriers, including limited cellular uptake across the apical membrane (Jiang, G. et al. *Hum. Gene. Ther.* 9:1531-1542 (1998), Matsui, H. et al., *J. Biol. Chem.* 272:1117-1126 (1997)), unproductive intracellular trafficking (Ferrari, S. et al. *Adv. Drug Deliv. Rev.* 54:1373-1393 (2002)), carrier toxicity, and immunogenicity (Ferrari, S. et al. *Clin. Exp. Immunol.* 132:1-8 (2003). A largely overlooked barrier to effective gene therapies for CF patients is the highly adhesive and hyperviscoelastic CF sputum that can immobilize and trap gene carriers, thereby greatly reducing the flux of gene carriers that can reach the airway epithelium, or exclude them altogether (Lai, S. K. et al. *Adv. Drug Deliv. Rev.* 61:158-171 (2009), Sanders, N. N. et al.

*Am. J. Respir. Crit. Care Med.* 162:1905-1911 (2000), Suk, J. S. et al. Biomaterials. 30:2591-2597 (2009)).

CF sputum is composed of a dense mesh of mucin fibers, large macromolecules containing a high density of negatively charged glycans interspersed with periodic hydrophobic regions (Lai, S. K. et al. *Adv. Drug Deliv. Rev.* 61:158-171 (2009), Cone, R. A. *Adv. Drug Deliv. Rev.* 61:75-78 (2009)). Elevated levels of bacterial and endogenous DNA, as well as actin filaments from degraded neutrophils in CF sputum, further contribute to its dense mesh structure and increased adhesivity (Sanders, N. et al. *Adv. Drug Deliv. Rev.* 61:115-127 (2009), Voynow, J. A. and Rubin, B. K. *Chest.* 135:505-512 (2009)). The average pore size in CF sputum has been estimated at 145±50 nm (range: 60-300 nm) (Suk, J. S. et al. *Biomaterials.* 30:2591-2597 (2009)), markedly smaller than the 340±70 nm for healthy human mucus secretions (Lai, S. K. et al. *Proc. Natl. Acad. Sci. U.S.A.* 107:598-603 (2010)). As a consequence of the elevated adhesivity and tighter mesh size, existing viral (Hida, K. et al. *PLoS ONE.* 6:e19919 (2011)) and non-viral (Suk, J. S., et al. *Mol. Ther.* 19:1981-1989 (2010)) gene carriers are extensively immobilized within CF sputum, suggesting that the inability to penetrate CF sputum may explain the limited success of gene therapies for CF.

In order to successfully deliver genetic therapies to the lungs of CF patients and patients with other lung diseases such as asthma, COPD and lung cancers, or other regions having mucus barriers to entry such as the gastrointestinal and reproductive tracts, gene carriers which can penetrate highly adhesive mucus and not elicit an immune response are required.

Therefore, it is an object of the invention to provide vehicles for efficient gene delivery through mucus by improved diffusion through the mucus without eliciting significant immunogenicity.

SUMMARY OF THE INVENTION

Nanoparticle gene carriers which exhibit increased rates of diffusion through mucus, as well as methods of making and using thereof, have been developed. The nanoparticle gene carriers are formed from a nucleic acid complexed to one or more biocompatible, polycationic polymers, mixed with one or more mucus resistant/diffusive polymers.

The cationic polymer can be any synthetic or natural polymer bearing at least two positive charges per molecule and having sufficient charge density and molecular size to bind to nucleic acid under physiological conditions. In certain embodiments, the polycationic polymer contains one or more amine residues, such as polyethylene imine (PEI) or a polyamino acid such as polyornithine, polyarginine, and polylysine. In preferred embodiments, the polycationic polymer is PEI. The molecular weight of the polycationic polymer can be varied in view of the identity of the one or more nucleic acids, the presence and identity of the other polymers present in the nanoparticle gene carrier. In some cases, the polycationic polymer has a molecular weight of between about 5,000 Daltons and about 100,000 Daltons, more preferably between about 5,000 and about 50,000 Daltons, most preferably between about 10,000 and about 35,000 Daltons.

The one or more polycationic polymers are present in the nanoparticle carrier in an amount effective to complex with one or more nucleic acids to form a particle having the desired particle size. In certain embodiments, the relative amount of the one or more polycationic polymers and the one or more nucleic acids can be represented by the number of nitrogen atoms in the one or more polycationic polymers divided by the number of phosphorous atoms in the one or more nucleic acids (N/P ratio). In certain embodiments, the one or more polycationic polymers and one or more nucleic acids are present at an N/P ratio of between about 2 and about 15, more preferably between about 3 and about 12, most preferably between about 4 and about 9. In preferred embodiments, the one or more polycationic polymers and one or more nucleic acids are present at an N/P ratio of about 6.

Nanoparticle gene carriers also contain one or more mucus resistant/diffusive polymers, i.e., polymers which facilitate passage through mucus, including CF mucus. Examples of suitable mucus-resistant/diffusive polymers include poly(alkylene glycols) such as polyethylene glycol (PEG), poly(propylene glycol) (PPG), and copolymers of ethylene glycol and propylene glycol. In certain cases, the mucus-resistant/diffusive polymer is a mucus-resistant/diffusive graft copolymer. Mucus-resistant/diffusive graft copolymers are branched copolymers containing a polymeric backbone functionalized by one or more mucus-resistant/diffusive polymeric side chains. In preferred embodiments, the mucus-resistant/diffusive polymer is a graft copolymer composed of a polymeric backbone functionalized by one or more poly(alkylene glycol) side chains. The poly(alkylene glycol) chains may contain between 8 and 500 repeat units, more preferably between 40 and 300 repeat units, most preferably between 40 and 200 repeat units. In certain embodiments, each of the mucus-resistant/diffusive polymeric sidechains has a molecular weight of between about 1 kDa and about 20 kDa, more preferably between about 1 kDa and about 15 kDa, most preferably between about 1 kDa and about 10 kDa. In a preferred embodiment, each of the mucus-resistant/diffusive polymeric sidechains has a molecular weight of about 5 kDa. Suitable poly (alkylene glycols) include PEG, polypropylene 1,2-glycol, polypropylene oxide), polypropylene 1,3-glycol, and copolymers thereof. In certain embodiments, the one or more poly(alkylene glycol) side chains are PEG chains.

The polymeric backbone of the mucus-resistant/diffusive graft copolymer may be hydrophobic or hydrophilic; however, preferably it is hydrophilic. The backbone of the mucus-resistant/diffusive graft copolymer can be polyanionic, polycationic, or neutrally charged at physiological pH. In some embodiments, the backbone of the mucus-resistant/diffusive graft copolymer is a polycationic polymer. In preferred embodiments, the backbone of the mucus-resistant/diffusive graft copolymer is PEI, or a polyamino acid such as polyornithine, polyarginine, and polylysine.

The density of grafted polymeric sidechains on the polymeric backbone of the mucus-resistant/diffusive graft copolymers will influence the surface chemistry of the nanoparticle gene carriers ultimately formed using the mucus-resistant/diffusive graft copolymer. Preferably, the grafting ratio of the graft copolymer is sufficiently high to provide nanoparticles that exhibit significant amounts of a mucus-resistant/diffusive polymer, such as PEG, on their surface to ensure a near zero surface charge and enhance diffusivity through mucus. In certain embodiments, the ratio of mucus-resistant/diffusive polymeric sidechains to polymer backbone in the mucus-resistant/diffusive graft copolymer is between about 10:1 and about 80:1, more preferably between about 20:1 and about 70:1, most preferably between about 30:1 and about 50:1. In certain embodiments, the ratio of mucus-resistant/diffusive polymeric sidechains to polymer backbone in the mucus-resistant/diffusive graft copolymer is between about 40:1. In preferred embodiments, the mucus-resistant/diffusive polymer is a mucus-resistant/diffusive graft copolymer composed of a PEI backbone functionalized by one or more PEG side chains. In particularly preferred embodiment, the nanoparticle gene carrier is a nanoparticle formed from one or more nucleic acids, PEI, and a mucus-resistant/diffusive graft copolymer composed of a PEI backbone functionalized by one or more PEG side chains.

The polycationic polymers and mucus-resistant/diffusive polymers can be incorporated into the nanoparticle gene carriers at varying molar ratios. In certain embodiments, the one or more polycationic polymers and one or more mucus-resistant/diffusive polymers are present in a molar ratio of between 1:5 and 5:1 (moles polycationic polymer:moles mucus-resistant/diffusive polymer), more preferably 1:4 and 4:1, more preferably between 1:4 and 3:1, most preferably between 1:3 and 3:1. In certain embodiments, the one or more polycationic polymers and one or more mucus-resistant/diffusive polymers are present in a molar ratio of 1:3 (moles polycationic polymer:moles mucus-resistant/diffusive polymer).

The nanoparticles are used for delivery of nucleic acid, including DNA, RNA, nucleic acid modified to increase resistance to nucleases and to increase stability, nucleic acid encoding or complementary to genes, and nucleic acid such as triple helix forming oligonucleotides which can be used to correct gene defects. One or more non-nucleic acid therapeutic agents can be incorporated into the nanoparticle gene carriers. Suitable additional active agents include, but are not limited to mucus degrading agents, bronchodilators, anti-inflammatory drugs, and anti-infective agents. In particular embodiments, the nanoparticle gene carriers include a mucus degrading agent such as N-acetylcysteine (NAC), denufosol.

Nanoparticle gene carriers can possess the necessary physiochemical properties to facilitate their diffusion through mucus, including particle size and surface charge. Generally, the nanoparticle gene carriers have a diameter which is smaller than the average pore size in normal or CF mucus. In certain embodiments, the nanoparticle gene carriers possess a diameter of between about 5 nm and about 500 nm, more preferably between about 5 nm and about 300 nm, more preferably between about 5 nm and about 150 nm, most preferably between about 5 nm and about 100 nm. In certain embodiments, the nanoparticle gene carriers possess a diameter of between about 40 nm and about 60 nm.

In order to facilitate their diffusion through mucus, the nanoparticle gene carriers possess a near neutral surface charge. In certain embodiments, the nanoparticle gene carriers possess a $\zeta$-potential of between about 10 mV and about −10 mV, more preferably between about 5 mV and about −5 mV, more preferably between about 3 mV and about −3 mV.

In certain embodiments, the nanoparticle gene carriers retain their particle size and $\zeta$-potential after nebulization or storage for at least 1 month, more preferably at least 2 months, most preferably at least 3 months at 4° C.

Nanoparticle gene carriers effectively protect the one or more nucleic acids incorporated therein from degradation during particle storage and delivery. In certain embodiments, the nanoparticle gene carriers prevent the complete digestion of cargo DNA when incubated with DNase at a concentration of 5 IU per 1 μg cargo DNA for a period of 1 hour, more preferably for a period of 2 hours, most preferably for a period of 3 hours at physiological conditions.

Nanoparticle gene carriers are able to rapidly and effectively diffuse through mucus. In some embodiments, the nanoparticle gene carriers exhibit geometric averaged mean square displacement (<MSD>) of greater than 0.01 $\mu m^2/$, more preferably greater than about 0.5 $\mu m^2/s$, most preferably greater than about 1 $\mu m^2/s$ in CF mucus as measured using the multiple particle tracking (MPT) method described in Example 2.

The degree to which a particle's diffusion through a medium, such as CF mucus, is impeded can be quantified in terms of an $\alpha$ value in freshly obtained and undiluted human mucus. An $\alpha$ value of 1 indicates unhindered Brownian motion in mucus whereas an $\alpha$ value of between 0 and 1 indicates hindered diffusion in mucus, with higher degree of obstruction being indicated by a lower $\alpha$ value. In certain embodiments, nanoparticle gene carriers exhibit an $\alpha$ value of greater that about 0.4, more preferably greater than about 0.5, more preferably greater than about 0.6, more preferably greater than about 0.7, most preferably greater than about 0.8 in mucus.

In certain embodiments, at least 30%, more preferably at least 40%, most preferably at least 50% of a population of nanoparticle gene carriers diffuse across a 10 μm thick sputum layer within one hour, determined by mathematical modeling estimates based on measured diffusion coefficients that were measured over the period of a few seconds.

In preferred embodiments, the nanoparticle gene carriers are substantially non-cytotoxic and do not elicit an inflammatory response when administered to the tissue of a patient.

Pharmaceutical formulations can be administered to any mucosal surface in a patient to treat or lessen one or more symptoms. Generally, the formulations are administered to the pulmonary tract. Aerosolized pharmaceutical formulations can be delivered to the lungs, preferably using a device, such as a dry powder inhaler, nebulizer, or pressurized metered dose inhaler (pMDI). Liquid formulations can also be administered to the respiratory tract by other suitable methods such as intranasal instillation, intratracheal instillation, and intratracheal injection. The formulations can also be administered to other mucosal surfaces including nasal, buccal, rectal and vaginal surfaces.

In certain embodiments, nanoparticle gene carriers are administered in an effective amount to increase the amount of CFTR present in the apical membrane of respiratory and non-respiratory epithelial cells. In preferred embodiments, nanoparticle gene carriers are administered in an effective amount to induce absent CFTR activity in a patient suffering from CF or augment the existing level of residual CFTR activity in a patient suffering from CF. In other embodiments the nucleic acid is used to treat cancers, other types of metabolic and pulmonary diseases, and for delivery via the nasal, buccal, rectal or vaginal route.

BRIEF DESCRIPTION OF THE DRAWINGS

FIG. 1A is a bar graph illustrating the $\zeta$-potential (mV) of nanoparticle gene carriers formed by condensing $PEG_{5k}$-PEI, PEI, and DNA at varying nitrogen to phosphate (N/P) ratios (3, 6, 9 and 12) and molar ratios of PEI to $PEG_{5k}$-PEI (0% $PEG_{5k}$-PEI, 100% PEI; 3:1 moles $PEG_{5k}$-PEI:moles PEI, 75% $PEG_{5k}$-PEI; 1:1 moles $PEG_{5k}$-PEI:moles PEI, 50% $PEG_{5k}$-PEI; and 100% $PEG_{5k}$-PEI, 0% PEI). FIG. 1B is a bar graph, illustrating the diameter (nm) of nanoparticle gene carriers formed by condensing PEG$_{5k}$-PEI, PEI, and DNA at varying nitrogen to phosphate (N/P) ratios (3, 6, 9 and 12) and molar ratios of PEI to PEG$_{5k}$-PEI (0% PEG$_{5k}$-PEI, 100% PEI; 3:1 moles PEG$_{5k}$-PEI:moles PEI, 75% PEG$_{5k}$-PEI; 1:1 moles PEG$_{5k}$-PEI:moles PEI, 50% PEG$_{5k}$-PEI; and 100% PEG$_{5k}$-PEI, 0% PEI). The error bars in FIGS. 1A-B indicate standard deviations of three independent measurements. The black and grey arrows in FIGS. 1A-B indicate the ζ-potential and size of nanoparticle gene carriers for PEI/DNA and PEG$_{5k}$-PEI/DNA used in the in vitro and in vivo experiments described in Examples 1 and 2.

FIG. 2A illustrates representative trajectories of nanoparticle gene carriers in CF sputum and CF sputum pretreated with NAC over a 20 second period (PEI/DNA in CF sputum, top left; PEG$_{5k}$-PEI/DNA in CF sputum, top right; and PEG$_{5k}$-PEI/DNA in CF sputum and CF sputum pretreated with NAC, bottom). The representative trajectories are plotted against a 1.25 μm scale bar. The inset figure (top left) plots the representative trajectory of PEI/DNA in CF sputum against a 125 nm scale bar. FIG. 2B is a graph plotting the averaged mean square displacement (<MSD>) in μm$^2$ as a function of time (τ, seconds) for PEI/DNA in CF sputum (solid line), PEG$_{5k}$-PEI/DNA in CF sputum (dashed line) and PEG$_{5k}$-PEI/DNA in CF sputum and CF sputum pretreated with NAC (dotted line). FIG. 2C plots the percent of nanoparticle gene carriers (PEI/DNA in CF sputum, top panel; PEG$_{5k}$-PEI/DNA in CF sputum, middle panel; and PEG$_{5k}$-PEI/DNA in CF sputum and CF sputum pretreated with NAC, bottom panel) which exhibited various effective diffusivities (<D$_{eff}$>, plotted in FIG. 2C as the Log$_{10}$ (D$_{eff}$)). FIG. 2D is a graph plotting the percent of nanoparticle gene carriers (PEI/DNA in CF sputum, solid line; PEG$_{5k}$-PEI/DNA in CF sputum, dashed line; and PEG$_{5k}$-PEI/DNA in CF sputum and CF sputum pretreated with NAC, dotted line) which will diffuse across a 10 μm thick CF sputum layer as a function of time (in hours).

FIG. 4A illustrates the percent lung retention of PEI/DNA (white bar) and PEG$_{5k}$-PEI/DNA (gray bar) nanoparticle gene carriers at 0 hours, 2 hours, and 6 hours after administration. FIG. 4B illustrates the percent gastrointestinal localization of PEI/DNA (white bar) and PEG$_{5k}$-PEI/DNA (gray bar) nanoparticle gene carriers at 0 hours, 2 hours, and 6 hours after administration. Both PEI/DNA and PEG$_{5k}$-PEI/DNA were distributed in both mouse lungs and upper GI tracts immediately after their intranasal administration. As shown in FIG. 4A, the total fluorescence of PEG$_{5k}$-PEI/DNA was well preserved in mouse lungs up to 6 hours post-administration, whereas that of PEI/DNA was sharply dropped to approximately 30% of the initial value at 2 hours post-administration, showing PEI/DNA was rapidly eliminated from the mouse lungs. As shown in FIG. 4B, the total fluorescence of PEI/DNA in the upper GI tract was sharply increased at 2 hours post-administration, whereas that of PEG$_{5k}$-PEI/DNA was gradually decreased over time.

FIG. 7A plots the percent cell viability of human bronchial epithelial cells (BEAS-2B) after incubation with varying concentrations (in μg/well) of PEI/DNA (circles) and PEG$_{5k}$-PEI/DNA (squares). FIG. 7B plots the percent cell viability of human alveolar epithelial cells (A549) after incubation with varying concentrations (in μg/well) of PEI/DNA (circles) and PEG$_{5k}$-PEI/DNA (squares). PEG$_{5k}$-PEI/DNA did not induce cytotoxicity at all doses tested regardless, whereas PEI/DNA exhibited dose-dependent increase in cytotoxicity in the both cell lines.

DETAILED DESCRIPTION OF THE INVENTION

I. Definitions

Figure 1A:
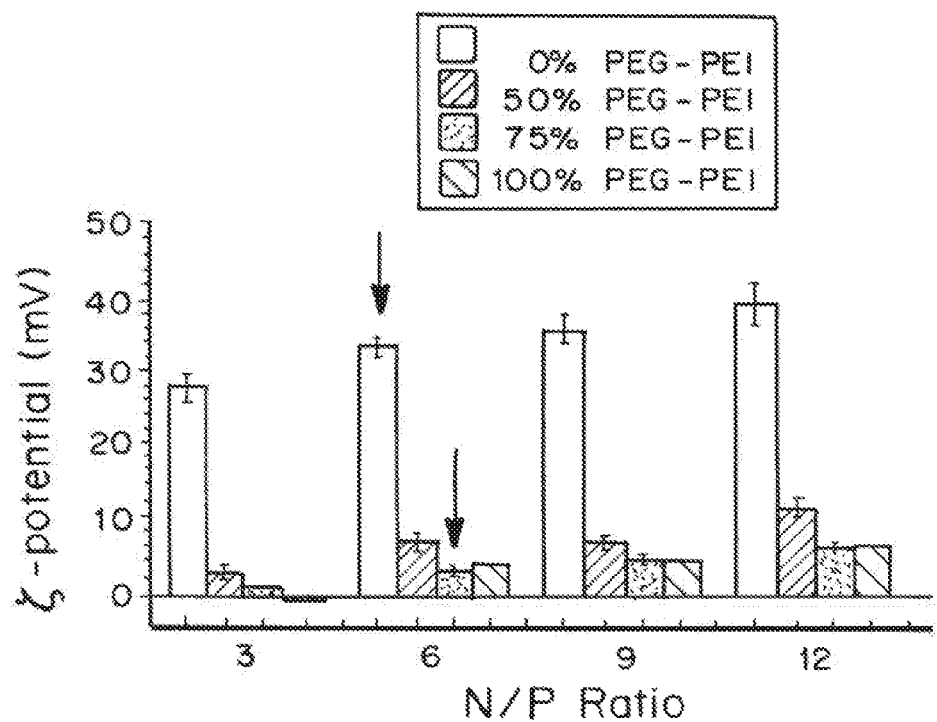
FIGS. 1A-B illustrate the physiochemical characteristics of nanoparticle gene carriers formed by condensing $PEG_{5k}$-PEI, PEI, and DNA at varying nitrogen to phosphate (N/P) ratios (3, 6, 9 and 12) and molar ratios of PEI to $PEG_{5k}$-PEI (0% $PEG_{5k}$-PEI, 100% PEI; 3:1 moles $PEG_{5k}$-PEI:moles PEI, 75% $PEG_{5k}$-PEI; 1:1 moles $PEG_{5k}$-PEI:moles PEI, 50% $PEG_{5k}$-PEI; and 100% $PEG_{5k}$-PEI, 0% PEI).

"Nanoparticle," as used herein, generally refers to a particle of any shape having a diameter from about 1 nm up to, but not including, about 1 micron, more preferably from about 5 nm to about 500 nm, most preferably from about 5 nm to about 100 nm. Nanoparticles can have any shape. Nanoparticles having a spherical shape are generally referred to as "nanospheres".

"Mean particle size," as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Mass Median Aerodynamic Diameter" (MMAD), as used herein, refers to the median aerodynamic size of a plurality of particles. The "aerodynamic diameter" is the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. MMAD can be experimentally determined by methods known in the art, such as by cascade impaction.

"Tap Density," as used herein, refers to a measure of the density of a powder. Tap density can be determined using the method of USP Bulk Density and Tapped Density, United States Pharmacopia convention, Rockville, Md., 10th Supplement, 4950-4951, 1999. Features which can contribute to low tap density include irregular surface texture and porous structure.

"Monodisperse" and "homogeneous size distribution," are used interchangeably herein and describe a plurality of nanoparticles or microparticles where the particles are the same or nearly aerodynamic diameter. As used herein, a monodisperse distribution refers to particle distributions in which 90% of the distribution lies within 5% of the mass median aerodynamic diameter.

"Pulmonary administration," as used herein, refers to administration of a pharmaceutical formulation containing an active agent into the lungs by inhalation. As used herein, the term "inhalation" refers to intake of air to the alveoli. The intake of air can occur through the mouth or nose. The intake of air can occur by self-administration of a formulation while inhaling, or by administration via a respirator to a patient on a respirator.

"Pharmaceutically acceptable," as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

"Biocompatible" and "biologically compatible," as used herein, generally refer to materials that are, along with any metabolites or degradation products thereof, generally nontoxic to the recipient, and do not cause any significant adverse effects to the recipient Generally speaking, biocompatible materials are materials which do not elicit a significant inflammatory or immune response when administered to a patient.

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

"Mucus," as used herein, refers to a viscoelastic natural substance containing primarily mucin glycoproteins and other materials, which protects epithelial surface of various organs/tissues, including respiratory, nasal, cervicovaginal, gastrointestinal, rectal, visual and auditory systems. "Sputum," as used herein, refers to highly viscoelastic mucus secretions consist of a variety of macromolecules such as DNA, actins and other cell debris released from dead cells in addition to mucin glycoproteins. "Sputum" is generally present in the pathogenic airways of patients afflicted by obstructive lung diseases, including but not limited to asthma, COPD and CF. "CF mucus" and "CF sputum," as used herein, refer to mucus and sputum, respectively, from a patient suffering from cystic fibrosis.

"Mucus Degrading Agent," as used herein, refers to a substance which increases the rate of mucus clearance when administered to a patient. Mucus degrading agents are known in the art. See, for example, Hanes, J. et al. *Gene Delivery to the Lung*, in *Pharmaceutical Inhalation Aerosol Technology*, Marcel Dekker, Inc., New York: 489-539 (2003). Examples of mucus degrading agents include N-acetylcysteine (NAC), which cleaves disulfide and sulfhydryl bonds present in mucin. Other mucus degrading agents include mugwort, bromelain, papain, clerodendrum, acetylcysteine, bromhexine, carbocisteine, eprazinone, mesna, ambroxol, sobrerol, domiodol, denufosol, letosteine, stepronin, tiopronin, gelsolin, thymosin β4, neltenexine, erdosteine, and various DNases including rhDNase.

"CF Mucus-resistant/diffusive Particle," as used herein, refers to a particle which exhibits reduced or low mucoadhesion in CF mucus and which therefore passes through the CF mucus at a higher rate than other particles. Such particles may be characterized as having high diffusivity through CF mucus. In certain embodiments, CF mucus-resistant/diffusive particles possess an effective diffusivity in CF mucus of greater than about 0.01 $\mu m^2/s$, more preferably greater than about 0.5 $\mu m^2/s$, most preferably greater than about 1 $\mu m^2/s$. In preferred embodiments, a population of particles may be characterized as "CF mucus-resistant/diffusive" if at least 30%, more preferably at least 40%, most preferably at least 50% of the population of particles diffuse across a 10 μm thick CF sputum layer within one hour.

"Cystic Fibrosis" (CF), as used herein, refers to an inherited genetic disease resulting from one or more mutations in the gene encoding the cystic fibrosis transmembrane conductance regulator (CFTR). In patients with cystic fibrosis, mutations in CFTR endogenously expressed in respiratory epithelia lead to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, result in death. Sequence analysis of the CFTR gene of CF chromosomes has revealed a variety of disease causing mutations. To date, more than 1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70 percent of the cases of cystic fibrosis and is associated with a severe disease. Cystic fibrosis affects approximately one in every 2,500 infants in the United States.

"Cystic Fibrosis Transmembrane Conductance Regulator" (CFTR), as used herein, refers to a transmembrane protein critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The gene encoding CFTR has been identified and sequenced. See Gregory, R. J. et al. *Nature* 347:382386 (1990); Rich, D. P. et al. Nature 347:358-362 (1990), and Riordan, J. R. et al. Science 245:1066-1073 (1989).

"Nucleic Acid," as used herein, refers to DNA, RNA, and nucleic acid molecules modified to increase stability for a variety of therapeutic purposes. One example is a gene encoding the human cystic fibrosis transmembrane conductance regulator (CFTR) protein, analogs and variants thereof, that can be expressed in CF individuals to correct at least in part some of the symptoms characteristic of CF. This also include molecules such as DNA fragments including regions for introducing corrections or modifications into the gene, such as triple helix forming DNA, that can be used to correct the endogenous CF gene in at least some of the CF patient's genes. It should be noted that this term is not limited to CFTR genes but applied to every geneticmaterials that can be used to treat, diagnose or cure disease.

II. Nanoparticle Gene Carriers

Nanoparticle gene carriers are polymeric nanoparticles formed from one or more polycationic polymers, one or more mucus-resistant/diffusive polymers, and one or more nucleic acids. One or more non-nucleic acid active agents can optionally be incorporated into the nanoparticle gene carriers.

The constituent polycationic polymers, mucus-resistant/diffusive polymers, and nucleic acids can be incorporated in varying ratios in order to provide particles with the desired physiochemical properties to facilitate diffusion through CF mucus, including particle size and surface charge.

In certain embodiments, one or more polycationic polymers are present in the nanoparticle carrier in an amount effective to complex with one or more nucleic acids to form a particle having the desired particle size. The one or more polycationic polymers and one or more nucleic acids can be incorporated into the nanoparticle gene carriers at varying ratios by weight. In certain embodiments, the polycationic polymer possesses one or more amine residues which are positively charged at physiological conditions. In these embodiments, the relative amount of the one or more polycationic polymers and one or more nucleic acids can be represented by the number of nitrogen atoms in the one or more polycationic polymers divided by the number of phosphorous atoms in the one or more nucleic acids (N/P ratio). In certain embodiments, the one or more polycationic polymers and one or more nucleic acids are present at an N/P ratio of between about 2 and about 15, more preferably between about 3 and about 12, most preferably between about 4 and about 9. In preferred embodiments, the one or more polycationic polymers and one or more nucleic acids are present at an N/P ratio of about 6.

The polycationic polymers and mucus-resistant/diffusive polymers can be incorporated into the nanoparticle gene carriers at varying molar ratios. In certain embodiments, the one or more polycationic polymers and one or more mucus-resistant/diffusive polymers are present in a molar ratio of between 1:5 and 5:1 (moles polycationic polymer:moles mucus-resistant/diffusive polymer), more preferably 1:4 and 4:1, more preferably between 1:4 and 3:1, most preferably between 1:3 and 3:1. In certain embodiments, the one or more polycationic polymers and one or more mucus-resistant/diffusive polymers are present in a molar ratio of 1:3 (moles polycationic polymer:moles mucus-resistant/diffusive polymer).

Nanoparticle gene carriers possess the necessary physiochemical properties to facilitate their diffusion through mucus, including particle size and surface charge. Generally, the nanoparticle gene carriers have a diameter which is smaller than the average pore size in normal or CF mucus. In certain embodiments, the nanoparticle gene carriers possess a diameter of between about 5 nm and about 500 nm, more preferably between about 5 nm and about 300 nm, more preferably between about 5 nm and about 150 nm, most preferably between about 5 nm and about 100 nm. In certain embodiments, the nanoparticle gene carriers possess a diameter of between about 40 nm and about 60 nm.

In certain embodiments, the nanoparticle gene carriers possess a surface with a relatively high poly(alkylene glycol) density. The presence of a high density of a poly (alkylene glycol), such as PEG, on the surface of the nanoparticle gene carriers. In some cases, the nanoparticle gene carriers surface poly(alkylene glycol) density of greater than about 0.5 poly(alkylene glycol) chains/nm$^2$, more preferably greater than about 0.75 poly(alkylene glycol) chains/nm$^2$, most preferably greater than about 1.0 poly(alkylene glycol) chains/nm$^2$.

In order to facilitate their diffusion through mucus, the nanoparticle gene carriers possess a near neutral surface charge. In certain embodiments, the nanoparticle gene carriers possess a ζ-potential of between about 10 mV and about −10 mV, more preferably between about 5 mV and about −5 mV, more preferably between about 3 mV and about −3 mV, most preferably between about 2 mV and about −2 mV.

In certain embodiments, the nanoparticle gene carriers retain their particle size and ζ-potential after nebulization or storage for at least 1 month, more preferably at least 2 months, most preferably at least 3 months at 4° C.

Nanoparticle gene carriers effectively protect the one or more nucleic acids incorporated therein (i.e., cargo DNA) from degradation during particle storage and delivery. In certain embodiments, the nanoparticle gene carriers prevent the complete digestion of cargo DNA when incubated with DNase at a concentration of 5 IU per 1 μg cargo DNA for a period of 1 hour, more preferably for a period of 2 hours, most preferably for a period of 3 hours at physiological conditions.

Nanoparticle gene carriers are able to rapidly and effectively diffuse through mucus. In some embodiments, the nanoparticle gene carriers exhibit geometric averaged mean square displacement (<MSD>) of greater than 0.01 μm$^2$/, more preferably greater than about 0.5 μm$^2$/s, most preferably greater than about 1 μm$^2$/s if CF mucus as measured using the multiple particle tracking (MPT) method described in Example 2.

The degree to which a particle's diffusion through a medium, such as CF mucus, in impeded can be quantified in terms of an α value. The α value for a particle can be calculated by displacement data collected using the MPT method to the equation below $$<MSD>=4D_o\tau^\alpha$$

where $D_o$ is diffusivity, <MSD> is the geometric averaged mean square displacement, $\tau$ is time, and $\alpha$ is an exponent equal to or less than 1 ($\alpha=1$ for pure Brownian diffusion; $0<\alpha<1$ for hindered diffusion with higher degree of obstruction being indicated by a lower $\alpha$ value). In certain embodiments, nanoparticle gene carriers exhibit an $\alpha$ value of greater that about 0.4, more preferably greater than about 0.5, more preferably greater than about 0.6, more preferably greater than about 0.7, most preferably greater than about 0.8 in CF mucus.

In certain embodiments, at least 30%, more preferably at least 40%, most preferably at least 50% of a population of nanoparticle gene carriers diffuse across a 10 μm thick CF sputum layer within one hour.

In preferred embodiments, the nanoparticle gene carriers substantially non-cytotoxic and do not elicit an inflammatory response when administered to the tissue of a patient.

A. Polycationic Polymers

Nanoparticle gene carriers include one or more biocompatible, polycationic polymers which complex with the nucleic acid cargo.

The cationic polymer can be any synthetic or natural polymer bearing at least two positive charges per molecule and having sufficient charge density and molecular size so as to bind to nucleic acid under physiological conditions (i.e., pH and salt conditions encountered within the body or within cells). In certain embodiments, the polycationic polymer contains one or more amine residues.

Suitable cationic polymers include, for example, polyethylene imine (PEI), polyallylamine, polyvinylamine, polyvinylpyridine, aminoacetalized polyvinyl alcohol), acrylic or methacrylic polymers (for example, poly(N,N-dimethylaminoethylmethacrylate)) bearing one or more amine residues, polyamino acids such as polyornithine, polyarginine, and polylysine, protamine, cationic polysaccharides such as chitosan, DEAE-cellulose, and DEAE-dextran, and polyamidoamine dendrimers (cationic dendrimer), as well as copolymers and blends thereof. In preferred embodiments, the polycationic polymer is PEI.

Cationic polymers can be either linear or branched, can be either homopolymers or copolymers, and when containing amino acids can have either L or D configuration, and can have any mixture of these features. Preferably, the cationic polymer molecule is sufficiently flexible to allow it to form a compact complex with one or more nucleic acid molecules.

In some embodiments, the polycationic polymer has a molecular weight of between about 5,000 Daltons and about 100,000 Daltons, more preferably between about 5,000 and about 50,000 Daltons, most preferably between about 10,000 and about 35,000 Daltons.

B. Mucus-Resistant/Diffusive Polymers

Nanoparticle gene carriers also include one or more mucus resistant/diffusive polymers. Mucus-resistant/diffusive polymers are polymers which render a nanoparticle mucus-resistant/diffusive when coated on the surface of the nanoparticle. Preferably, mucus-resistant/diffusive polymers are neutrally charged.

Mucus-resistant/diffusive polymers can be mixed with, dispersed in, or otherwise non-covalently associated with the other components forming the nanoparticle gene carrier. Mucus-resistant/diffusive polymers can also be covalently conjugated to the surface of a nanoparticle gene carrier.

Examples of suitable mucus-resistant/diffusive polymers include, but are not limited to, poly(alkylene glycols) such as polyethylene glycol (PEG), poly(propylene glycol) (PPG), and copolymers of ethylene glycol and propylene glycol.

In certain embodiments, the mucus-resistant/diffusive polymer contains one or more poly(alkylene glycol) chains. The poly(alkylene glycol) chains may contain between 8 and 500 repeat units, more preferably between 40 and 300 repeat units, most preferably between 40 and 200 repeat units. Suitable poly(alkylene glycols) include PEG, polypropylene 1,2-glycol, poly(propylene oxide), polypropylene 1,3-glycol, and copolymers thereof. In certain embodiments, the mucus-resistant/diffusive polymer contains one or more PEG chains. In such cases, the PEG chains can be linear or branched, such as those described in U.S. Pat. No. 5,932,462. In certain embodiments, the PEG chains are linear.

In preferred embodiments, the mucus-resistant/diffusive polymer is a mucus-resistant/diffusive graft copolymer. Mucus-resistant/diffusive graft copolymers are branched copolymers containing a polymeric backbone functionalized by one or more mucus-resistant/diffusive polymeric side chains, in which the side chains are structurally distinct from the polymeric backbone. In these embodiments, both the polymeric backbone and the polymeric side chains may individually be homopolymers or copolymers. Furthermore, the one or more polymeric sidechains may have the same or different polymeric composition.

In preferred embodiments, the mucus-resistant/diffusive polymer is a graft copolymer composed of a polymeric backbone functionalized by one or more poly(alkylene glycol) side chains. The poly(alkylene glycol) chains may contain between 8 and 500 repeat units, more preferably between 40 and 300 repeat units, most preferably between 40 and 200 repeat units. Suitable poly(alkylene glycols) include PEG, polypropylene 1,2-glycol, polypropylene oxide), polypropylene 1,3-glycol, and copolymers thereof. In certain embodiments, the one or more poly(alkylene glycol) side chains are PEG chains. In such cases, the PEG chains can be linear or branched.

In these embodiments, each mucus-resistant/diffusive polymeric side chain independently has a molecular weight of about 300 Da to 1 MDa. Each mucus-resistant/diffusive polymeric side chain may have a molecular weight ranging between the molecular weights listed above. In certain embodiments, each of the mucus-resistant/diffusive polymeric sidechains a molecular weight of between about 1 kDa and about 20 kDa, more preferably between about 1 kDa and about 15 kDa, most preferably between about 1 kDa and about 10 kDa. In a preferred embodiment, each of the mucus-resistant/diffusive polymeric sidechains has a molecular weight of about 5 kDa.

The polymeric backbone of the mucus-resistant/diffusive graft copolymer may be hydrophobic or hydrophilic; however, preferably it is hydrophilic. The backbone of the mucus-resistant/diffusive graft copolymer can be polyanionic, polycationic, or neutrally charged at physiological pH. In some embodiments, the backbone of the mucus-resistant/diffusive graft copolymer is a polycationic polymer. In preferred embodiments, the backbone of the mucus-resistant/diffusive graft copolymer is PEI, or a polyamino acid such as polyornithine, polyarginine, and polylysine.

The density of grafted polymeric sidechains on the polymeric backbone of the mucus-resistant/diffusive graft copolymers will influence the surface chemistry of the nanoparticle gene carriers ultimately formed using the mucus-resistant/diffusive graft copolymer. Preferably, the grafting ratio of the graft copolymer is sufficiently high to provide nanoparticles that exhibit significant amounts of a mucus-resistant/diffusive polymer, such as PEG, on their surface to ensure a near zero surface charge and enhance diffusivity through mucus.

In certain embodiments, the ratio of mucus-resistant/diffusive polymeric sidechains to polymer backbone in the mucus-resistant/diffusive graft copolymer is between about 10:1 and about 80:1, more preferably between about 20:1 and about 70:1, most preferably between about 30:1 and about 50:1. In certain embodiments, the ratio of mucus-resistant/diffusive polymeric sidechains to polymer backbone in the mucus-resistant/diffusive graft copolymer is between about 40:1. In preferred embodiments, the mucus-resistant/diffusive polymer is a mucus-resistant/diffusive graft copolymer composed of a PEI backbone functionalized by one or more PEG side chains. In particularly preferred embodiment, the nanoparticle gene carrier is a nanoparticle formed from one or more nucleic acids, PEI, and a mucus-resistant/diffusive graft copolymer composed of a PEI backbone functionalized by one or more PEG side chains.

In preferred embodiments, the mucus-resistant/diffusive polymer is a mucus-resistant/diffusive graft copolymer composed of a PEI backbone functionalized by one or more PEG side chains.

C. Nucleic Acids

Nanoparticle gene carriers typically carry one or more nucleic acids. The nucleic acid can alter, correct, or replace an endogenous nucleic acid sequence. In preferred embodiments, the nucleic acid encodes a normal cystic fibrosis transmembrane conductance regulator (CFTR). In other preferred embodiments, the nucleic acid is used to treat cancers, correct defects in genes in other pulmonary diseases and metabolic diseases affecting lung function, genes such as those for the treatment of Parkinsons and ALS where the genes reach the brain through nasal delivery.

Gene therapy is a technique for correcting defective genes responsible for disease development. Researchers may use one of several approaches for correcting faulty genes:

A normal gene may be inserted into a nonspecific location within the genome to replace a nonfunctional gene. This approach is most common.

An abnormal gene could be swapped for a normal gene through homologous recombination.

The abnormal gene could be repaired through selective reverse mutation, which returns the gene to its normal function.

The regulation (the degree to which a gene is turned on or off) of a particular gene could be altered.

The nucleic acid carried by the nanoparticle gene carrier can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. For example, the nucleic acid can be custom synthesized to contain properties that are tailored to fit a desired use. Common modifications include, but are not limited to use of locked nucleic acids (LNAs), unlocked nucleic acids (UNAs), morpholinos, peptide nucleic acids (PNA), phosphorothioate linkages, phosphonoacetate linkages, propyne analogs, 2'-O-methyl RNA, 5-Me-dC, 2-5' linked phosphodiester linage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. P. et al., Organic Chem., 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Phosphorothioates (or S-oligos) are a variant of normal DNA in which one of the nonbridging oxygens is replaced by a sulfur. The sulforization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one 1,1-dioxide (BDTD). The latter methods avoid the problem of elemental sulfur's insolubility in most organic solvents and the toxicity of carbon disulfide. The TETD and BDTD methods also yield higher purity phosphorothioates. (See generally Uhlmann and Peymann, 1990, Chemical Reviews 90, at pages 545-561 and references cited therein, Padmapriya and Agrawal, 1993, Bioorg. & Med. Chem. Lett. 3, 761).

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

In some embodiments, the nucleic acid includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl)uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2-modified analogs such as, but not limited to O-methyl, amino-, and fluoro-modified analogs. Inhibitory RNAs modified with 2-flouro (2'-F) pyrimidines appear to have favorable properties in vitro. Moreover, one report recently suggested 2'-F modified siRNAs have enhanced activity in cell culture as compared to 2-OH containing siRNAs. 2'-F modified siRNAs are functional in mice but that they do not necessarily have enhanced intracellular activity over 2'-OH siRNAs.

In some embodiments the nucleic acid includes one or more sugar moiety modifications, including, but are not limited to, 2'-O-aminoethoxy, 2'-O-amonioethyl (2'-OAE), 2'-O-methoxy, 2'-O-methyl, 2-guanidoethyl (2'-OGE), 2'-O, 4'-C-methylene (LNA), 2'-O-(methoxyethyl) (2'-OME) and 2'-O—(N-(methyl)acetamido) (2'-OMA).

Nanoparticle gene carriers carrying one or more nucleic acid can be utilized to deliver nucleic acid cargo in a method of gene therapy. Methods of gene therapy typically rely on the introduction into the cell of a nucleic acid molecule that alters the genotype of the cell. Introduction of the nucleic acid molecule can correct, replace, or otherwise alters the endogenous gene via genetic recombination. Methods can include introduction of an entire replacement copy of a defective gene, a heterologous gene, or a small nucleic acid molecule such as an oligonucleotide. For example, corrective gene can be introduced into a non-specific location within the host's genome, this approach typically requires delivery systems to introduce the replacement gene into the cell, such as genetically engineered viral vectors.

Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences necessary elements for the translation and/or transcription of the inserted coding sequence. For example, the coding sequence is preferably operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

Viral vectors include adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a Kd less than 10-6, 10-8, 10-10, or 10-12.

Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406. Highly stable PNA:DNA:PNA triplex structures can be formed from strand invasion of a duplex DNA with two PNA strands. In this complex, the PNA/DNA/PNA triple helix portion and the PNA/DNA duplex portion both produce displacement of the pyrimidine-rich triple helix, creating an altered structure that has been shown to strongly provoke the nucleotide excision repair pathway and to activate the site for recombination with the donor oligonucleotide. Two PNA strands can also be linked together to form a bis-PNA molecule. The triplex-forming molecules are useful to induce site-specific homologous recombination in mammalian cells when used in combination with one or more donor oligonucleotides which provides the corrected sequence. Donor oligonucleotides can be tethered to triplex-forming molecules or can be separate from the triplex-forming molecules. The donor oligonucleotides can contain at least one nucleotide mutation, insertion or deletion relative to the target duplex DNA.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406. Pseudocomplementary oligonucleotides are complementary oligonucleotides that contain one or more modifications such that they do not recognize or hybridize to each other, for example due to steric hindrance, but each can recognize and hybridize to complementary nucleic acid strands at the target site. In some embodiments, pseudocomplementary oligonucleotides are pseudocomplemenary peptide nucleic acids (pcPNAs). Pseudocomplementary oligonucleotides can be more efficient and provide increased flexibility over methods of induced recombination such as triple-helix oligonucleotides and bis-peptide nucleic acids which require a polypurine sequence in the target double-stranded DNA.

D. Additional Active Agents

Nanoparticle gene carriers can carry only "genetic" materials. Others can be co-delivered depending on the application. However, any "genetic" materials that can perform the listed functions can be packaged in the nanoparticles. For example, tumor suppressor genes such as p53 and Rb can be complexed into nanoparticles to be used for lung cancer patients, so as any plasmid DNA or siRNA that possess anti-inflammatory, anti-viral functions, etc.

Nanoparticle gene carriers can optionally contain one or more additional, non-nucleic acid active agents. The one or more additional active agents can be dispersed in the nanoparticle gene carriers or be covalently attached to one or more of the polymeric components of the nanoparticle Suitable additional active agents include, but are not limited, to other nucleic acid-based medicine, mucus degrading agents, bronchodilators, anti-inflammatory drugs, antiproliferatives, chemotherapeutics, vasodilators, and anti-infective agents.

Nanoparticle gene carriers can optionally contain one or more mucus degrading agents. Suitable mucus degrading agents include N-acetylcysteine (NAC), mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4, neltenexine, erdosteine, denufosol, and various DNases including rhDNase (such as Dornase Alfa, sold under the tradename PULMOZYME® by Genentech), although care should be taken to deliver DNase separate from DNA.

Nanoparticle gene carriers can optionally contain one or more anti-infective agents. In certain embodiments, the nanoparticle gene carriers contain one or more antibiotics, such as tobramycin, colistin, or aztreonam.

Nanoparticle gene carriers can optionally contain one or more inhaled corticosteroids, such as flunisolide, triamcinolone acetonide, beclomethasone dipropionate, mometasone, budesonide, ciclesonide, or fluticasone propionate.

Nanoparticle gene carriers can optionally contain one or more antibiotics which are known to possess anti-inflammatory activity, such as erythromycin, azithromycin, or clarithromycin.

Nanoparticles may also be used for the delivery of chemotherapeutic agents, and antiproliferative agents.

III. Methods of Nanoparticle Formation and Pharmaceutical Formulations

A. Nanoparticle Formation

Nanoparticle gene carriers can be formed from one or more cationic polymers, one or more mucus-resistant/diffusive polymers, and one or more nucleic acids using any suitable method for the formation of polymer nanoparticles known in the art. The method employed for nanoparticle formation will depend on a variety of factors, including the characteristics of the polymers present in the nanoparticle gene carrier, as well as the desired particle size and size distribution.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing nanoparticles gene carriers include, but are not limited to, solvent evaporation, solvent removal, spray drying, phase inversion, low temperature casting, and nanoprecipitation. Suitable methods of particle formulation are briefly described below. Pharmaceutically acceptable excipients, including pH modifying agents, disintegrants, preservatives, and antioxidants, can optionally be incorporated into the particles during particle formation. As described above, one or more additional active agents can also be incorporated into the nanoparticle gene carrier during particle formation.

In spray drying, the components of the nanoparticle gene carrier are dispersed or dissolved in a suitable solvent. The solution is pumped through a micronizing nozzle driven by a flow of compressed gas, and the resulting aerosol is suspended in a heated cyclone of air, allowing the solvent to evaporate from the microdroplets, forming particles.

Methods for very low temperature casting of nanoparticles are described in U.S. Pat. No. 5,019,400 to Gombotz et al. In this method, the components of the nanoparticle gene carrier are dispersed or dissolved is a solvent. The mixture is then atomized into a vessel containing a liquid non-solvent at a temperature below the freezing point of the solution which freezes the components of the nanoparticle gene carrier as tiny droplets. As the droplets and non-solvent for the components are warmed, the solvent in the droplets thaws and is extracted into the non-solvent, hardening the nanoparticles.

In nanoprecipitation, a solution containing one or more nucleic acids is added dropwise to a solution containing the polymeric components of the nanoparticle gene carrier. As the nucleic acids are complexed by the cationic polymers, nanoparticles precipitate from solution. The resulting nanoparticles are isolated from solution, for example by filtration or centrifugation, washed, and dried using a lyophilizer.

B. Pharmaceutical Formulations

Formulations contain an effective amount of nanoparticle carriers in a pharmaceutical carrier appropriate for administration to a mucosal surface. Pharmaceutical formulations and methods for the pulmonary administration of active agents to patients are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

Formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

A. Dry Powder Formulations

Dry powder formulations are finely divided solid formulations containing nanoparticle carriers which are suitable for pulmonary administration. Dry powder formulations include, at a minimum, one or more nanoparticle carriers which are suitable for pulmonary administration. Such dry powder formulations can be administered via pulmonary inhalation to a patient without the benefit of any carrier, other than air or a suitable propellant.

In other embodiments, the dry powder formulations contain one or more nanoparticle gene carriers in combination with a pharmaceutically acceptable carrier. In these embodiments, the nanoparticle gene carriers and pharmaceutical carrier can be formed into nano- or microparticles for delivery to the lung.

The pharmaceutical carrier may include a bulking agent or a lipid or surfactant. Natural surfactants such as dipalmitoylphosphatidylcholine (DPPC) are the most preferred. Synthetic and animal derived pulmonary surfactants include:

Synthetic Pulmonary Surfactants

Exosurf—a mixture of DPPC with hexadecanol and tyloxapol added as spreading agents Pumactant (Artificial Lung Expanding Compound or ALEC)—a mixture of DPPC and PG KL-4—composed of DPPC, palmitoyl-oleoyl phosphatidylglycerol, and palmitic acid, combined with a 21 amino acid synthetic peptide that mimics the structural characteristics of SP-B.

Venticute—DPPC, PG, palmitic acid and recombinant SP-C

Animal Derived Surfactants

Alveofact—extracted from cow lung lavage fluid

Curosurf—extracted from material derived from minced pig lung

Infasurf—extracted from calf lung lavage fluid

Survanta—extracted from minced cow lung with additional DPPC, palmitic acid and tripalmitin Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more nanoparticle carriers with one or more pharmaceutically acceptable carriers. Optionally, additional active agents may be incorporated into the mixture as discussed below. The mixture is then formed into particles suitable for pulmonary administration using techniques known in the art, such as lyophilization, spray drying, agglomeration, spray coating, coacervation, low temperature casting, milling (e.g., air-attrition milling (jet milling), ball milling), high pressure homogenization, and/or supercritical fluid crystallization.

An appropriate method of particle formation can be selected based on the desired particle size, particle size distribution, and particle morphology desired for the formulation. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung. Accordingly, dry powder formulations is processed into particles having the appropriate mass median aerodynamic diameter (MMAD), tap density, and surface roughness to achieve delivery of the one or more active agents to the desired region(s) of the lung. For example, preferred particle morphologies for delivery to the deep lung are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e. about 0.5 to about 3 microns), are capable of efficiently reaching the alveolar region. Particles having diameters smaller than about 0.5 microns can also be deposited in the alveolar region by sedimentation.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodyanamic diameter for maximum deposition within the lungs can be calculated. See, for example, U.S. Pat. No. 7,052,678 to Vanbever, et al.

Microparticles cannot diffuse through mucus even if their surface is muco-resistant. However, mucus-penetrating gene carriers can be encapsulated in microparticles to impact upper lung, and subsequently release nanoparticle gene carriers. In some embodiments, the dry powder formulation is composed of a plurality of particles having a median mass aerodynamic diameter between about 0.05 to about 10 microns, more preferably between about 0.05 microns to about 7 microns, most preferably between about 0.05 to about 5 microns. In some embodiments, the dry powder formulation is composed of a plurality of particles having a median mass aerodynamic diameter between about 0.05 microns to about 3 microns, more preferably between about 0.05 microns to about 1 micron, more preferably between about 0.05 microns to about 0.7 microns. In some embodiments, the dry powder formulation is composed of a plurality of particles having a median mass aerodynamic diameter between about 3 to about 5 microns. In some embodiments, the dry powder formulation is composed of a plurality of particles having a median mass aerodynamic diameter between about 5 to about 7 microns. In some embodiments, the dry powder formulation is composed of a plurality of particles having a median mass aerodynamic diameter between about 7 to about 9.5 microns.

In some cases, there may be an advantage to delivering particles larger than about 3 microns in diameter. Phagocytosis of particles by alveolar macrophages diminishes precipitously as particle diameter increases beyond about 3 microns. Kawaguchi, H., et al., Biomaterials 7: 61-66 (1986); Krenis, L. J. and Strauss, B., Proc. Soc. Exp. Med., 107: 748-750 (1961); and Rudt, S. and Muller, R. H., J. Contr. Rel, 22:263-272 (1992). By administering particles with an aerodynamic volume greater than 3 microns, phagocytic engulfment by alveolar macrophages and clearance from the lungs can be minimized.

In some embodiments, at least about 80%, more preferably at least about 90%, most preferably at least about 95% of the particles in dry powder formulation have aerodynamic diameter of less than about 10 microns, more preferably less than about 7 microns, most preferably about 5 microns. In some embodiments, at least about 80%, more preferably at least about 90%, most preferably at least about 95% of the particles in dry powder formulation have aerodynamic diameter of greater than about 0:03 microns.

In some embodiments, at least about 80%, more preferably at least about 90%, most preferably at least about 95% of the particles in dry powder formulation have aerodynamic diameter of greater than about 0.03 microns and less than about 10 microns, more preferably greater than about 0.03 microns and less than about 7 microns, most preferably greater than about 0.03 microns and less than about 5 microns. In some embodiments, at least about 80%, more preferably at least about 90%, most preferably at least about 95% of the particles in dry powder formulation have aerodynamic diameter of greater than about 0.03 microns and less than about 3 microns. In some embodiments, at least about 80%, more preferably at least about 90%, most preferably at least about 95% of the particles in dry powder formulation have aerodynamic diameter of greater than about 0.03 microns and less than about 5 microns. In some embodiments, at least about 80%, more preferably at least about 90%, most preferably at least about 95% of the particles in dry powder formulation have aerodynamic diameter of greater than about 0.03 microns and less than about 7 microns. In some embodiments, at least about 80%, more preferably at least about 90%, most preferably at least about 95% of the particles in dry powder formulation have aerodynamic diameter of greater than about 0.03 microns and less than about 9.5 microns.

In some embodiments, the particles have a tap density of less than about 0.4 g/cm$^3$, more preferably less than about 0.25 g/cm$^3$, most preferably less than about 0.1 g/cm$^3$. Features which can contribute to low tap density include irregular surface texture and porous structure.

In some cases, the particles are spherical or ovoid in shape. The particles can have a smooth or rough surface texture. The particles may also be coated with a polymer or other suitable material to control release of one or more active agents in the lungs.

Dry powder formulations can be administered as dry powder using suitable methods known in the art. Alternatively, the dry powder formulations can be suspended in the liquid formulation s described below, and administered to the lung using methods known in the art for the delivery of liquid formulations.

B. Liquid Formulations

Liquid formulations contain one or more nanoparticle carriers suspended in a liquid pharmaceutical carrier.

Suitable liquid carriers include, but are not limited to distilled water, de-ionized water, pure or ultrapure water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human.

Preferably, liquid formulations are isotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl-p-hydroxybenzoate.

In some cases the liquid formulation may contain one or more solvents that are low toxicity organic (i.e. nonaqueous) class 3 residual solvents, such as ethanol, acetone, ethyl acetate, tetrahydofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

C. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

Preferably, a dry powder or liquid formulation as described above is formulated into aerosol formulations using one or more propellants. Suitable propellants include air, hydrocarbons, such as pentane, isopentane, butane, isobutane, propane and ethane, carbon dioxide, chlorofluorocarbons, fluorocarbons, and combinations thereof. Suitable fluorocarbons include 1-6 hydrogen containing fluorocarbons, such as $CHF_2CHF_2$, $CF_3CH_2F$, $CH_2F_2CH_3$, and $CF_3CHFCF_3$ as well as fluorinated ethers such as $CF_3$—O—$CF_3$, $CF_2H$—O—$CHF_2$, and $CF_3$—$CF_2$—O—$CF_2$—$CH_3$. Suitable fluorocarbons also include perfluorocarbons, such as 1-4 carbon perfluorocarbons including $CF_3CF_3$, $CF_3CF_2CF_3$, and $CF_3CF_2CF_2CF_3$.

Preferably, the propellants include, but not limited to, one or more hydrofluoroalkanes (HFA). Suitable HFA propellants, include but are not limited to, 1,1,1,2,3,3,-heptafluoro-n-propane (HFA 227), 1,1,1,2-tetrafluoroethane (HFA 134) 1,1,1,2,25 3,3,3-heptafluoropropane (Propellant 227), or any mixture of these propellants.

Preferably, the one or more propellants have sufficient vapor pressure to render them effective as propellants. Preferably, fee one or more propellants are selected so that the density of the mixture is matched to the density of the particles in the aerosol formulation in order to minimize settling or creaming of the particles in the aerosol formulation. The propellant is preferably present in an amount sufficient to propel a plurality of the selected doses of the aerosol formulation from an aerosol canister.

IV. Methods of Use

Pharmaceutical formulations contain nanoparticle carriers in a pharmaceutical carrier appropriate for pulmonary administration. These are administered in dosages to patients to treat or lessen the severity of a disease. In one preferred embodiment, the patient has a mutant form of human CFTR which results in less than normal levels of CFTR function. In particular embodiments, the patient possesses one or more of the following mutations of human CFTR: ΔF50S, R117H, G551D, and combinations thereof.

A. Methods of Administration

Pharmaceutical formulations can be administered to any mucosal surface. Generally, the formulations are administered to the pulmonary tract. Aerosolized pharmaceutical formulations can be delivered to the lungs, preferably using one of the device described below.

Liquid formulations can also be administered to the respiratory tract by other suitable methods such as intranasal instillation, intratracheal instillation, and intratracheal injection.

1. Devices for Pulmonary Administration

In some cases, the one or more active agents are delivered into the lungs by inhalation of an aerosolized pharmaceutical formulation. Inhalation can occur through the nose and/or the mouth of the patient. Administration can occur by self-administration of the formulation while inhaling, or by administration of the formulation via a respirator to a patient on a respirator.

In some cases, a device is used to administer the formulations to the lungs. Suitable devices include, but are not limited to, dry powder inhalers, pressurized metered dose inhalers, nebulizers, and electrohydrodynamic aerosol devices.

Dry Powder Inhalers

The dry powder formulations described above can be administered to the lungs of a patient using a dry powder inhaler (DPI). DPI devices typically use a mechanism such as a burst of gas to create a cloud of dry powder inside a container, which can then be inhaled by the patient.

In a dry powder inhaler, the dose to be administered is stored in the form of a non-pressurized dry powder and, on actuation of the inhaler, the particles of the powder are inhaled by the subject. In some cases, a compressed gas (i.e., propellant) may be used to dispense the powder, similar to pressurized metered dose inhalers (pMDIs). In some cases, the DPI may be breath actuated, meaning that an aerosol is created in precise response to inspiration. Typically, dry powder inhalers administer a dose of less than a few tens of milligrams per inhalation to avoid provocation of cough.

DPIs function via a variety of mechanical means to administer formulations to the lungs. In some DPIs, a doctor blade or shutter slides across the dry powder formulation contained in a reservoir, culling the formulation into a flowpath whereby the patient can inhale the powder in a single breath. In other DPIs, the dry powder formulation is packaged in a preformed dosage form, such as a blister, tabule, tablet, or gelcap, which is pierced, crushed, or otherwise unsealed to release the dry powder formulation into a flowpath for subsequent inhalation. Still others DPIs release the dry powder formulation into a chamber or capsule and use mechanical or electrical agitators to keep the dry powder formulation suspended in the air until the patient inhales.

Dry powder formulations may be packaged in various forms, such as a loose powder, cake, or pressed shape for insertion in to the reservoir of a DPI.

Examples suitable DPIs for the administration of the formulations described above include the Turbohaler® inhaler (Astrazeneca, Wilmington, Del.), the Clickhaler® inhaler (Innovata, Ruddington, Nottingham, UK), the Diskus® inhaler (Glaxo, Greenford, Middlesex, UK), the Easy-Haler® (Orion, Expoo, FI), the Exubera® inhaler (Pfizer, New York, N.Y.), the Qdose® inhaler (Microdose, Monmouth Junction, N.J.), and the Spiros® inhaler (Dura, San Diego, Calif.).

Pressurized Metered Dose Inhalers

The liquid formulations described above can be administered to the lungs of a patient using a pressurized metered dose inhaler (pMDI).

Pressurized Metered Dose Inhalers (pMDIs) generally include at least two components: a canister in which the liquid formulation is held under pressure in combination with one or more propellants, and a receptacle used to hold and actuate the canister. The canister may contain a single or multiple doses of the formulation. The canister may include a valve, typically a metering valve, from which the contents of the canister may be discharged. Aerosolized drug is dispensed from the pMDI by applying a force on the canister to push it into the receptacle, thereby opening the valve and causing the drug particles to be conveyed from the valve through the receptacle outlet. Upon discharge from the canister, the liquid formulation is atomized, forming an aerosol.

pMDIs typically employ one or more propellants to pressurize the contents of the canister and to propel the liquid formulation out of the receptacle outlet, forming an aerosol. Any suitable propellants, including those discussed above, may be utilized. The propellant may take a variety of forms. For example, the propellant may be a compressed gas or a liquefied gas. Chlorofluorocarbons (CFC) were once commonly used as liquid propellants, but have now been banned. They have been replaced by the now widely accepted hydrofluororalkane (HFA) propellants.

pMDIs are available from a number of suppliers, including 3M Corporation, Aventis, Boehringer Ingleheim, Forest Laboratories, Glaxo-Wellcome, Schering Plough and Vectura. In some cases, the patient administers an aerosolized formulation by manually discharging the aerosolized formulation from the pMDI in coordination with inspiration. In this way, the aerosolized formulation is entrained within the inspiratory air flow and conveyed to the lungs.

In other cases, a breath-actuated trigger, such as that included in the Tempo® inhaler (MAP Pharmaceuticals, Mountain View, Calif.) may be employed that simultaneously discharges a dose of the formulation upon sensing inhalation. These devices, which discharge the aerosol formulation when the user begins to inhale, are known as breath-actuated pressurized metered dose inhalers (baMDIs).

Nebulizers

The liquid formulations described above can also be administered using a nebulizer. Nebulizers are liquid aerosol generators that convert the liquid formulation described able, usually aqueous-based compositions, into mists or clouds of small droplets, preferably having diameters less than 5 microns mass median aerodynamic diameter, which can be inhaled into the lower respiratory tract. This process is called atomization. The droplets carry the one Or more active agents into the nose, upper airways or deep lungs when the aerosol cloud is inhaled. Any type of nebulizer may be used to administer the formulation to a patient, including, but not limited to pneumatic (jet) nebulizers and electromechanical nebulizers.

Pneumatic (jet) nebulizers use a pressurized gas supply as a driving force for atomization of the liquid formulation. Compressed gas is delivered through a nozzle or jet to create a low pressure field which entrains a surrounding liquid formulation and shears it into a thin film or filaments. The film or filaments are unstable and break up into small droplets that are carried by the compressed gas flow into the inspiratory breath. Baffles inserted into the droplet plume screen out the larger droplets and return them to the bulk liquid reservoir. Examples of pneumatic nebulizers include, but are not limited to, PARI LC Plus®, PARI LC Sprint®, Devilbiss PulmoAide®, and Boehringer Ingelheim Respima®.

Electromechanical nebulizers use electrically generated mechanical force to atomize liquid formulations. The electromechanical driving force can be applied, for example, by vibrating the liquid formulation at ultrasonic frequencies, or by forcing the bulk liquid through small holes in a thin film. The forces generate thin liquid films or filament streams which break up into small droplets to form a slow moving aerosol stream which can be entrained in an inspiratory flow.

In some cases, the electromechanical nebulizer is an ultrasonic nebulizer, in which the liquid formulation is coupled to a vibrator oscillating at frequencies in the ultrasonic range. The coupling is achieved by placing the liquid in direct contact with the vibrator such as a plate or ring in a holding cup, or by placing large droplets on a solid vibrating projector (a horn). The vibrations generate circular standing films which break up into droplets at their edges to atomize the liquid formulation. Examples of ultrasonic nebulizers include DuroMist®, Drive Medical Beetle Neb®, Octive Tech Densylogic®, and John Bunn Nano-Sonic®.

In some cases, the electromechanical nebulizer is a mesh nebulizer, in which the liquid formulation is driven through a mesh or membrane with small holes ranging from 2 to 8 microns in diameter, to generate thin filaments which break up into small droplets. In certain designs, the liquid formulation is forced through the mesh by applying pressure with a solenoid piston driver (for example, the AERx® nebulizer), or by sandwiching the liquid between a piezoelectrically vibrated plate and the mesh, which results in a oscillatory pumping action (for example EFlow®, AerovectRx®, or TouchSpray® nebulizer). In other cases, the mesh vibrates back and forth through a standing column of the liquid to pump it through the holes. Examples of such nebilzers include the AeroNeb Go®, AeroNeb Pro®. PARI EFlow®, Omron 22UE®; and Aradigm AERx®.

Electrohydrodynamic Aerosol Devices

The liquid formulations described above can also be administered using an electrohydrodynamic (EHD) aerosol device. EHD aerosol devices use electrical energy to aerosolize liquid drug solutions or suspensions. Examples of EHD aerosol devices are known in the art. See, for example, U.S. Pat. No. 4,765,539 to Noakes et al. and U.S. Pat. No. 4,962,885 to Coffee, R. A.

The electrochemical properties of the formulation may be important parameters to optimize when delivering the liquid formulation to the lung with an EHD aerosol device and such optimization is routinely performed by one of skill in the art.

B. Dosages and Therapeutic Outcomes

The nanoparticle gene carriers are administered in an effective amount to cause expression of a normal gene product to supplement or replace a defective gene product, as measured by the alleviation of one or more symptom, or to kill cells such as tumor cells.

The nanoparticle gene carriers are administered in an effective amount to provide active or non-mutated CFTR in the apical membrane of respiratory and non-respiratory epithelial cells. In preferred embodiments, nanoparticle gene carriers are administered in an effective amount to induce absent CFTR activity in a patient suffering from CF or augment the existing level of residual CFTR activity in a patient suffering from CF.

The presence of residual CFTR activity at the epithelial surface can be readily detected using methods known in the art, including standard electrophysiological, biochemical, and/or histochemical techniques. Such methods identify and/or quantify CFTR activity using in vivo or ex vivo electrophysiological techniques, measurement of sweat or salivary CT concentrations, or ex vivo biochemical or histochemical techniques to monitor CFTR cell surface density.

C. Co-Administration

Nanoparticle gene carriers can optionally be co-administered with one or more additional active agents. Co-administration can include the simultaneous and/or sequential administration of the one or more additional active agents and the nanoparticle gene carriers. The one or more additional active agents and the nanoparticle gene carriers can be included in the same or different pharmaceutical formulation. The one or more additional active agents and the nanoparticle gene carriers can achieve the same or different clinical benefit. An appropriate time course for sequential administration may be chosen by the physician, according to such factors as the nature of a patient's illness, and the patient's condition. In certain embodiments, sequential administration includes the co-administration of one or more additional active agents and the nanoparticle gene earners within a period of one week, 72 hours, 48 hours, 24 hours, or 12 hours.

EXAMPLES

Example 1

Formation and Characterization of Nanoparticle Gene Carriers

Materials and Methods

Conjugation of PEG to PEI

Methoxy PEG N-hydroxysuccinimide (mPEG-NHS, 5 kDa, Sigma Aldrich, St. Louis, Mo.) was conjugated to 25 kDa branched PEI (Sigma Aldrich) to yield $PEG_{5k}$-PEI copolymer as follows. Briefly, PEI was dissolved in ultrapure distilled water and pH was adjusted to 7-8. Approximately 50 molar excess of mPEG-NHS was added to PEI solution and allowed to react overnight. After the reaction, the polymer solution was extensively dialyzed against ultrapure distilled water and then lyophilized. Nuclear magnetic resonance (NMR) was used to confirm a PEG:PEI ratio to be ~37. The lyophilized polymers were dissolved in ultrapure distilled water and pH was adjusted to ~7-7.5.

PEI-Based Gene Carrier Formulation

The plasmid pd1GL3-RL (7.9 kbp) containing two CMV-promoted luciferase genes were propagated in *Escherichia coli* DH5α (Kan/Neo selection). Plasmid DNA was collected and purified using Qiagen Endofree Giga Prep kits (Qiagen Inc., Valencia, Calif.) per manufacturer's protocol. For fluorescence microscopy/imaging studies, an aliquot of plasmids were covalently labeled with either Cy3 or Cy5 (Label IT® Nucleic Acid Labeling Kit, Mirus, San Francisco, Calif.).

Nanoparticle gene carriers were formed upon the dropwise addition of 10 parts (by volume) of plasmid DNA (0.2 mg/ml) to vortexing solution of 1 part (by volume) of polymer solution. The polymer solutions were prepared at varying nitrogen to phosphate (N/P) ratios (3, 6, 9 and 12) and molar ratios of PEI to $PEG_{5k}$-PEI (0, 50, 75 and 100% $PEG_{5k}$-PEI). For fluorescence imaging of gene carriers, 20% Cy3- or Cy5-labeled DNA (i.e., 80% unlabeled DNA) was used to assemble fluorescently labeled nanoparticle gene carriers. The mixture of DNA and polymer solution was incubated for 30 minutes at room temperature to form the nanoparticle gene carriers, and aggregates were removed by syringe filtration (0.2 μm). To remove free PEI, gene carriers were washed twice with 10 volume of ultrapure distilled water, and re-concentrated to 1 mg/ml using Amicon® Ultra Centrifugal Filters (100,000 MWCO, Millipore Corp., Billerica, Mass.). The concentration of DNA in the nanoparticle gene carriers was determined via absorbance at 260 nm, measured with a NanoDrop ND-1000 spectrophotometer (Nanodrop Technologies, Wilmington, Del.).

Physicochemical Characterization of PEI-Based Gene Carriers

Nanoparticle gene carriers were imaged using transmission electron microscopy (TEM, Hitachi H7600, Japan) to determine their morphology and size. The hydrodynamic diameter and ζ-potential of the nanoparticles was determined by dynamic light scattering and laser Doppler anemometry, respectively, using a Nanosizer ZS90 (Malvern Instruments, Southborough, Mass.).

Protection of cargo DNA against DNase digestion was assayed as follows. One microgram of DNA, either alone or compacted in gene carriers, was incubated with recombinant DNase I (2 or 5 IU per 1 µg DNA) (RNase free; Roche Diagnostics GmbH, Mannheim, Germany) at 37° C. for 2 h. After the treatment, DNase was inactivated by addition of 0.5 M EDTA followed by 15 minutes incubation at room temperature. To release DNA for gel electrophoresis, gene carriers were incubated with 10 µl of 1000 IU/ml of heparin solution (Sigma Aldrich, St. Louis, Mo.) at 37° C. for 30 min. Gel electrophoresis was carried out on a 0.8% agarose gel containing 50 µg/ml ethidium bromide for 30 min at 120 V.

Estimation of Surface PEG Density

The amount of plasmid DNA (pd1GL3-RL) in each nanoparticle gene carrier was estimated based on its hydrodynamic diameter. Previous studies report that a single 5.5 kb plasmid is fully compacted by cationic detergents to form a 35 nm spherical particle (Dauty, E. et al. *J. Am. Chem. Soc.* 123:9227-9234 (2001)), and particle size varies with the cubic root of DNA size (Blessing, T. et al. *Proc. Natl. Acad. Sci. USA.* 95:1427-1431 (1998)). The number of $PEG_{5k}$-PEI polymers in each gene carrier was estimated based on the N/P ratio necessary to fully compact plasmid DNA and the molar ratio of PEI to $PEG_{5k}$-PEI used for gene carrier formulation. Finally, the surface PEG density for each nanoparticle gene carrier was calculated by normalizing the total number of PEG polymers on each particle by the particle surface area.

Results 5 kDa PEG was grafted to 25 kDa branched PEI at a high PEG to PEI grafting ratio (~50:1).

Nanoparticles were formed by condensing 100% $PEG_{5k}$-PEI with DNA ($PEG_{5k}$-$PEI^{100\%}$/DNA) at varying N/P ratios to determine whether the high PEG content can effectively shield the highly positive surface charge generally observed with gene carriers prepared with unconjugated PEI only (PEI/DNA).

Figure 1B:
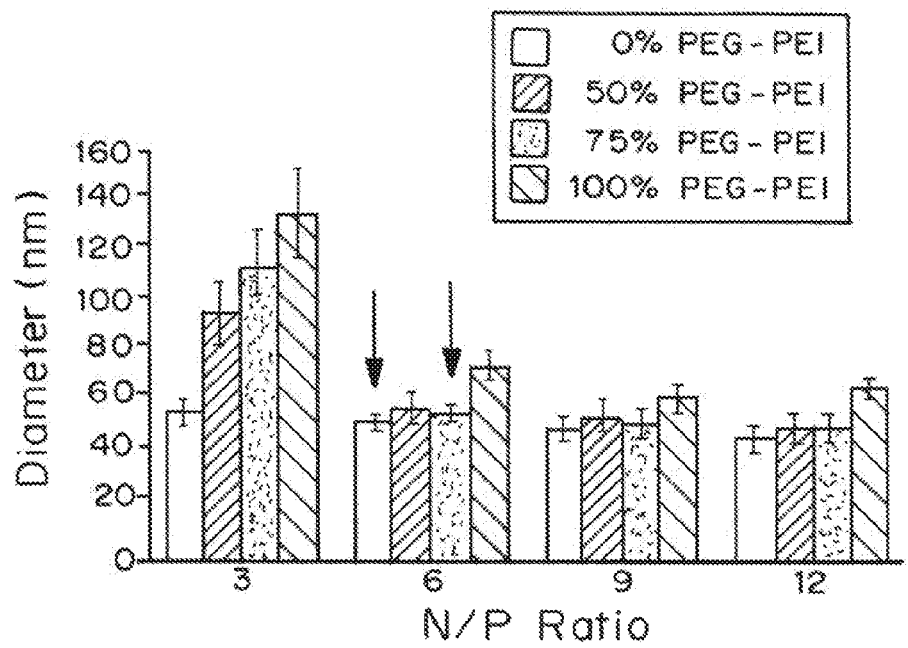

The surface charge of $PEG_{5k}$-$PEI^{100\%}$/DNA, as indicated by their potential, was significantly reduced to near neutral compared to PEI/DNA at all N/P ratios tested (FIG. 1A). However, sizes of $PEG_{5k}$-$PEI^{100\%}$/DNA at all N/P ratios were significantly larger than those of PEI/DNA at corresponding N/P ratios (FIG. 1B). This suggests that the large size of $PEG_{5k}$-$PEI^{100\%}$/DNA is a result of the steric hindrance of PEG which interferes with electrostatic interactions between DNA and PEI.

Nanoparticles formed by including different amounts of free, unconjugated PEI together with $PEG_{5k}$-PEI (i.e., different molar ratios of $PEG_{5k}$-PEI:PEI) were prepared. Nanoparticles were prepared at varying N/P ratios (3, 6, 9, and 12) and varying molar rations of $PEG_{5k}$-PEI:PEI (100% $PEG_{5k}$-PEI; 1:1 moles $PEG_{5k}$-PEI:moles PEI, 50% $PEG_{5k}$-PEI; 3:1 moles $PEG_{5k}$-PEI:moles PEI, 75% $PEG_{5k}$-PEI; and 0% $PEG_{5k}$-PEI, 100% PEI).

By including different amounts of free, unconjugated PEI together with $PEG_{5k}$-PEI, highly compacted yet neutrally charged gene carriers could be prepared. Nanoparticle gene carriers formulated at an N/P ratio of 6 and 75% $PEG_{5k}$-PEI ($PEG_{5k}$-$PEI^{75\%}$) ($PEG_{5k}$-PEI/DNA) were both (i) highly compacted, with hydrodynamic diameters comparable to PEI/DNA ~50 nm; FIG. 1B and Table 1), and (ii) nearly neutral in surface charge (FIG. 1A and Table 1). This suggests that the positive charge groups of PEI in the core of the nanoparticle gene carriers are effectively shielded by PEG polymers from $PEG_{5k}$-PEI in the periphery. $PEG_{5k}$-PEI/DNA retained its physicochemical properties (i.e., size and ζ-potential) after nebulization or storage for at least 1 month at 4° C.

TABLE 1

| Gene Carrier | Hydrodynamic Diameter (nm)[a] | ζ-potential (mV)[b] | NAC Treatment | $D_w/\langle D_{eff}\rangle$[c] | $\alpha$[d] | Penetrable Percentage (%)[e] |
|---|---|---|---|---|---|---|
| PEI/DNA | 52 ± 1.0 | 34 ± 1.0 | N/A | 7700 | 0.38 | 5 |
| $PEG_{5k}$-PEI/DNA | 56 ± 2.5 | 2.9 ± 0.5 | N/A | 110 | 0.78 | 48 |
| $PEG_{5k}$-PEI/DNA | 56 ± 2.5 | 2.9 ± 0.5 | 0.5M | 35 | 0.87 | 70 |

[a] Measured by dynamic light scattering (DLS). The error values indicated standard deviations of three independent measurements.
[b] Measured at pH 7.0. The error values indicate standard deviations of three independent measurements.
[c] $D_w$ is the theoretical diffusivity of particles in water calculated from the Stokes-Einstein equation and $\langle D_{eff}\rangle$ is measured at time scale of 1 second. The $D_w/\langle D_{eff}\rangle$ ratio indicates by what multiple the average particle movement rate in CF sputum is slower than in pure water.
[d] Calculated by fitting the experimental data for <MSD> (shown in FIG. 2B) to <MSD> = $4D_0\tau^\alpha$, where $D_0$ is diffusivity and $\alpha$ is anomalous exponent equal to or less than 1. The larger the negative deviation from 1, the higher the degree of hindrance to particle motion.
[e] Signifies the percentage of gene carriers that are expected to penetrate a 10 µM CF sputum layer in 20 minutes, which corresponds to the penetrable fraction at 20 minutes in FIG. 2D.

PEI/DNA and $PEG_{5k}$-PEI/DNA were incubated with DNase for 2 hours at concentrations of 2 and 5 IU per 1 ng DNA to determine their ability to protect nucleic acid cargo from degradation. $PEG_{5k}$-PEI/DNA provided robust protection of cargo DNA against DNase challenge for 2 h at a DNase concentration of 2 IU per 1 µg DNA. At a higher DNase concentration (5 IU per 1 µg DNA), while most of the DNA molecules in PEI/DNA were completely digested, DNA in $PEG_{5k}$-PEI/DNA remained partially protected, as reflected by the preservation of nicked circular DNA. These results suggest that $PEG_{5k}$-PEI/DNA likely offers superior protection of DNA payload compared to PEI/DNA.

Example 2

In Vitro and In Vivo Investigation of Nanoparticle Gene Carriers

Materials

CF Sputum Collection and Rheological Characterization

Sputum spontaneously expectorated from male and female CF patients (ages 24-37) was collected at the Johns Hopkins Adult Cystic Fibrosis Program. The procedures conformed to ethical standards of the Johns Hopkins Medicine Institutional Review Board. Samples were acquired from the weekly CF outpatient clinic, placed on ice upon collection and during transport, and studied the same day. The total number of individual samples used for the present studies was 4.

Treating CF Sputum with Mucolytic Agents

One molar solution of N-acetylcysteine (Sigma Aldrich) was prepared and adjusted to pH~7, since its mucolytic activity is optimal with a pH of 7.0-9.0. To study the effect of N-acetylcysteine (NAC) on the diffusion of nanoparticle gene carriers in CF sputum, sputum was treated with NAC (final concentration of 20 mM), for 30 min at 37° C. prior to the addition of fluorescently labeled nanoparticle gene carriers (2% dilution of CF sputum).

Multiple Particle Tracking in CF Sputum

Fluorescently labeled nanoparticle gene carriers were added to ~30 μl of CF sputum (3% dilution) with or without NAC pretreatment, transferred to custom-made 30 μl microwells, and equilibrated for 30 min at 37° C. prior to microscopy. The dynamics of nanoparticle gene carriers were quantified using multiple particle tracking (MPT; See, for example, Suk, J. S. et al. *Biomaterials*. 30:2591-2597 (2009), Lai, S. K. et al. *Proc. Natl. Acad. Sci. U.S.A.* 104:1482-1487 (2007), and Suh, J. et al. *Proc. Natl. Acad. Sci. U.S.A.* 100:3878-3882 (2003)). Briefly, 20 second movies at 67 ms temporal resolution were acquired using an Evolve 512 EMCCD camera (Photometrics, Tucson, Ariz.) equipped on an inverted epifluorescence microscope (Axio Observer D1, Zeiss; Thornwood, N.Y.) with 100×/1.4 NA objective. Movies were analyzed with Metamorph software (Universal Imaging, Glendale, Wis.) to extract x, y positional data for the fluorescently labeled nanoparticle gene carriers over time. Time-averaged mean square displacement (MSD) and effective diffusivity ($D_{eff}$) for individual gene carriers were calculated as a function of time scale (τ) (See, for example, Suh, J. et al. *Proc. Natl. Acad. Sci. U.S.A.* 100:3878-3882 (2003), Suh, J. et al. *Adv. Drug Deliv. Rev.* 57:1551 (2005), Suk, J. S. et al. *Exp. Biol. Med.* 232:461-469 (2007)). CF sputum was assumed to be locally isotropic but not necessarily homogeneous; thus, 2D diffusivity is equal to 3D diffusivity (Suh, J. et al. *Adv. Drug Deliv. Rev.* 57:1551 (2005)). Bulk transport properties were calculated by geometric ensemble-averaging of individual transport rates. The tracking resolution was 10 nm, determined by tracking displacement of particles immobilized with a strong adhesive (Apgar, J. et al. *Biophys. J.* 79:1095-1106 (2000)). Fractions of gene carriers expected to penetrate a 10 μm CF sputum layer was calculated as previously reported (See Suk, J. S. et al. *Biomaterials*. 30:2591-2597 (2009) and Tang, B. C. et al. *Proc. Natl. Acad. Sci. U.S.A.* 106:19268-19273 (2009))

In Vivo Airway Gene Transfer

Balb/c mice (female, 6-8 weeks), anesthetized in a perfusion chamber with 1-1.5% isoflurane at 1-1.5 L/min oxygen flow, were intranasally instilled with a variety of PEI-based gene carriers at a dose of 50 μg pd1GL3-RL (50 μl) per mouse. Mice treated with either saline or free DNA served as a control.

To quantify airway gene expression, the luciferease activity on lung tissue homogenates was measured. Briefly, mice were euthanized 24 h after the dosing with gene carriers, perfused their hearts with 3 ml 1×PBS, and harvested and ground lung tissues with a homogenizer (Power Gen 125; Fisher Scientific, Pittsburg, Pa.). The homogenates were subjected to three freeze-and-thaw cycles to assure complete cell lysis, and supernatants were obtained by centrifugation. Luciferase activity in the supernatant was then measured using a standard luciferase assay kit (Promega, Madison, Wis.) and a 20/20n luminometer (Turner Biosystems, Sunnyvale, Calif.). The relative light unit (RLU) was normalized with total protein content measured by bicinchoninic acid (BCA) assay.

Effect of NAC treatment on airway gene transfer by PEG-coated gene carriers was determined using methods known in the art (Suk, J. S., et al. *Mol. Ther.* 19:1981-1989 (2010). Briefly, C57 mice (female, 6-8 weeks), anesthetized in a perfusion chamber with 1-1.5% isoflurane at 1-1.5 L/min oxygen flow, were intranasally challenged twice with 50 μl of 2 mg/ml *P. aeruginosa* lipopolysaccharide (LPS) (Sigma) on day 0 and 2 (48 h interval) to induce airway mucus hypersecretion. Four days after the initial LPS challenge, C57 mice were anesthetized and intranasally treated with isotonic saline (control) or 0.5 M NAC, 30 min prior to dosing with gene carriers as described above. The level of airway gene transfer was determined as previously stated.

Diffusion and Distribution of PEI-Based Gene Carriers in Mucus of Mouse Trachea and Lung Parenchyma Balb/c mice (female, 6-8 weeks) were anesthetized and intranasally instilled with a variety of Cy3-labeled PEI-based gene carriers as described above. Twenty minutes later, each mouse was euthanized and a small piece of trachea (~5 mm) was dissected. The trachea was then cut open longitudinally, lay flat on a glass slide (mucosal side up), and sealed with a coverslip using a thin layer of super glue to minimize potential dehydration. Movies and images were acquired with a fluorescence microscope to qualitatively compare diffusion and distribution of different gene carriers in mucus of mouse trachea.

To investigate the distribution of gene carriers in mouse lung parenchyma, lungs of mice intranasally administered with a variety of Cy3-labeled gene carriers were dissected after 2 h. Lungs were then inflated with a 50:50 mixture of optimal cutting temperature compound (OCT) and 1×PBS, embedded in 100% OCT to be frozen with liquid $N_2$, and cryosectioned at −22° C. Subsequently, tissue sections were stained with ProLong® Gold antifade reagent with DAPI (Molecular Probes, Eugene, Oreg.) and images were captured with a fluorescence microscope.

Retention of PEI-Based Gene Carriers in Mouse Lung and Gastrointestinal Tract

Balb/c mice (female, 6-8 weeks) were anesthetized and intranasally instilled with a variety of Cy5-labeled PEI-based gene carriers as described above. At various time points (0, 2, and 6 h) after the administration of gene carriers, each mouse was euthanized and lung and upper gastrointestinal (GI) tract (i.e., esophagus and stomach) were harvested. Mice treated with saline served as control. Fluorescent images of individual lungs and upper GI tracts were then captured with a Xenogen IVIS spectrum optical imaging device (Caliper Life Sciences, Inc., Hopkinton, Mass.) at the exposure time of 1 second, and total photon counts (i.e., total fluorescence) were measured and subtracted with saline controls using Living Images® 2.5 software (Caliper Life Sciences, Inc.). Lung retention and upper GI localization of gene carriers over time were calculated by normalizing total photon counts at varying time points with initial photon counts.

Airway Inflammation Mediated by PEG-Based Gene Carriers

Balb/c mice (female, 6-8 weeks) were anesthetized and intranasally instilled with a variety of PEI-based gene carriers as described above. Mice treated with saline served as a control. Twenty four hours later, mice were euthanized, lung tissues were excised from the chest, and inflated with formalin and immersed overnight in formalin. Subsequently, lung tissues were paraffin-sectioned, stained for hematoxylin and eosin (H & E), and visualized using an inverted microscope, Nikon Eclipse E600 (Nikon Instruments, Melville, N.Y.). To quantify immune cell infiltration, mice were euthanized, lung tissues were excise from the chest without damaging trachea and lung tissue, and thin-end pipette tip attached to 1 ml syringe was inserted into the trachea. Bronchioalveolar lavage was performed ex vivo three times sequentially with 1 ml 1×PBD each time, and the bronchioalveolar lavage fluid (BALF) was pooled for each mouse. Cells were collected from the BALF by centrifuge at 2,000 rpm for 8 min, treated with ACK lysing buffer (Quality Biological, Inc., Gaithersburg, Md.) to remove red blood cells, and leukocytes were collected by centrifuge at 2,000 rpm for 8 min. Leukocytes were then resuspended in 1% paraformaldehyde and counted with a Coulter counter (Beckman, Brea, Calif.). Enzyme-linked immunosorbent assay (ELISA) was performed to determine the concentration of TNF-α in BALF. Briefly, 1 ml of the supernatants after the first centrifuge were transferred to microcentrifuge tubes, lyophilized overnight, and resuspended in 100 μl of distilled water. The concentration of TNF-α was then measured using mouse TNF-α immunoassay kit (R&D Systems Inc., Minneapolis, Minn.) per manufacturer's protocol.

In Vitro Cytotoxicity

Human bronchial (BEAS-2B) and alveolar (A549) epithelial cells were seeded on a 96 well plate at 10,000 cells/well. Varying concentrations of PEI-based gene carriers were added and incubated for 48 h at 37° C. After the incubation, cells were treated with 0.5 mg/ml MTT (3-(4,5-dimethyl-thiazol-2-yl)-2,5-diphenyl tetrazonlium bromide) solution for 4 h, and subsequently the solution was removed and replaced with DMSO. The cell viability was measured spectrophotometrically at 570 nm by using a microplate reader (BioTek Instuments, Inc., Winooski, Vt.).

Results

Inclusion of PEG-PEI Enhances Sputum Penetration by PEI-Based Gene Carriers.

To visualize the diffusion of nanoparticle gene carriers in CF sputum, nanoparticle gene carriers containing fluorescently labeled DNA were formulated. The diffusion of nanoparticle gene carriers through CF mucus was analyzed in vitro using MPT techniques. As expected from their highly positive surface charge, the motion of PEI/DNA was strongly hindered in sputum freshly expectorated by CF patients, evident by their highly constrained, non-Brownian time-lapse traces (FIG. 2A).

The translational motion of hundreds of PEI/DNA in CF sputum was quantified using MPT. The geometric averaged mean square displacement (<MSD>) of PEI/DNA in four different sputum samples was ~4.4×10$^{-3}$ μm$^2$ at the time scale (τ) of 1 second (FIG. 2B), equivalent to an effective diffusivity (<$D_{eff}$>) of ~1.1×10$^{-3}$ μm$^2$/s at the same time scale. For comparison, the theoretical effective diffusivity ($D_{eff}$) for a spherical particle with the same hydrodynamic diameter as PEI/DNA is ~8.7 μm$^2$/s in water, suggesting that PEI/DNA is slowed by at least ~8,000-fold on average in CF sputum compared to in water. To evaluate the extent of the impediment to carrier diffusion, we estimated the α value by fitting the transport data to the equation, <MSD>=4$D_o$τ$^α$, where $D_o$ is diffusivity and α is an exponent equal to or less than 1 (α=1 for pure Brownian diffusion; 0<α<1 for hindered diffusion with higher degree of obstruction for lower α value). The α value for PEI/DNA was 0.38 (Table 1), which is comparable to the value, previously found for latex nanoparticles shown to be permanently trapped in CF sputum (Suk, J. S. et al. *Biomaterials*. 30:2591-2597 (2009)). Individual $D_{eff}$ analysis showed that only a small fraction of gene earners showed high mobility; <9% of PEI/DNA exhibited $D_{eff}$ excess of 0.1 μm$^2$/s (top panel in FIG. 2C). Based on the measured $D_{eff}$ of hundreds of individual PEI and Fick's second law of diffusion, it can be estimated that less than 5% of PEI/DNA is expected to traverse a 10 μm thick CF sputum layer within 20 min (FIG. 2D and Table 1).

Figure 2A:
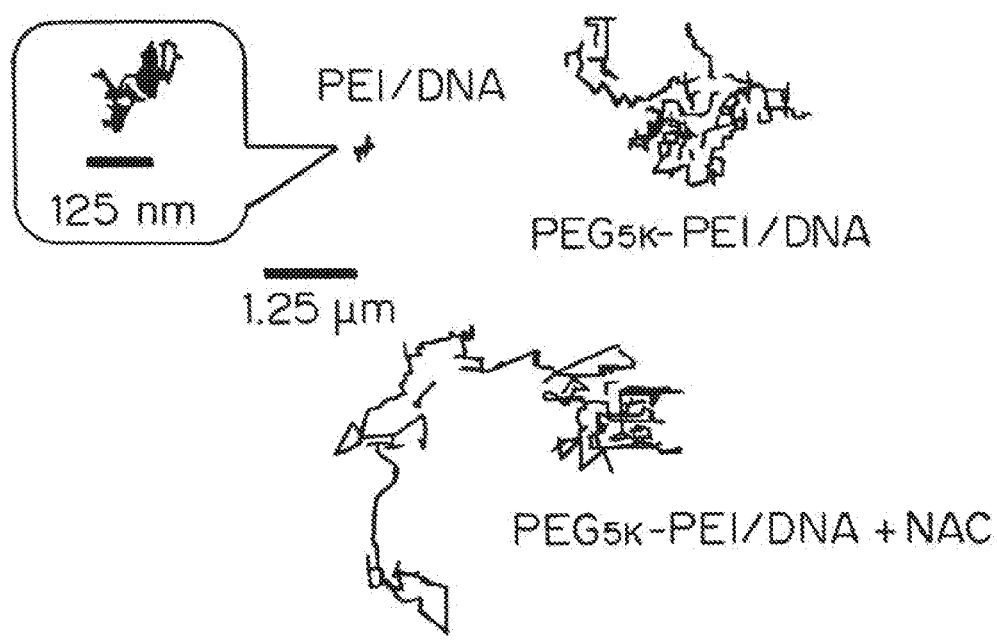
FIGS. 2A-2D illustrate the transport of PEI/DNA and PEG$_{5k}$-PEI/DNA gene carriers in native CF sputum and CF sputum pretreated with NAC.
Figure 2B:
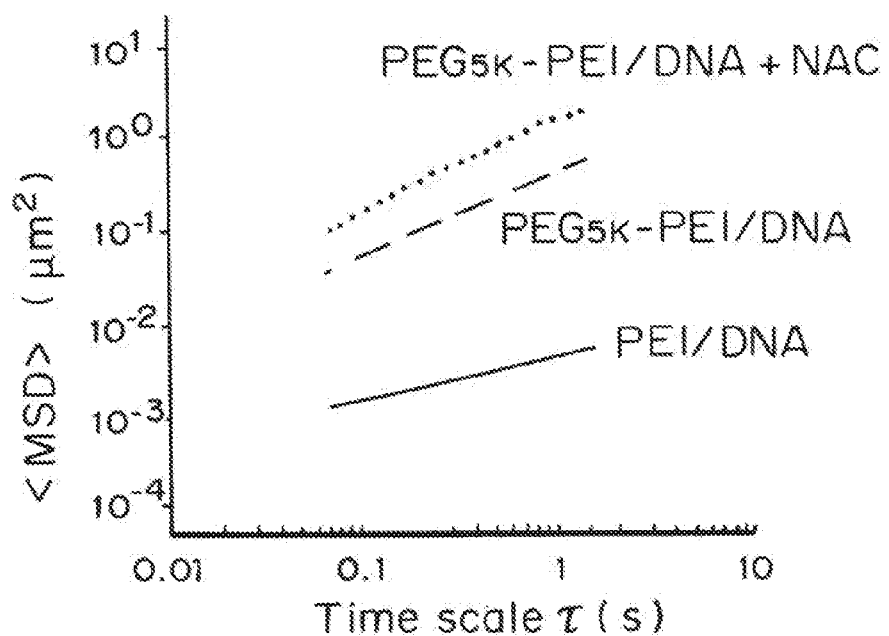
Figure 2C:
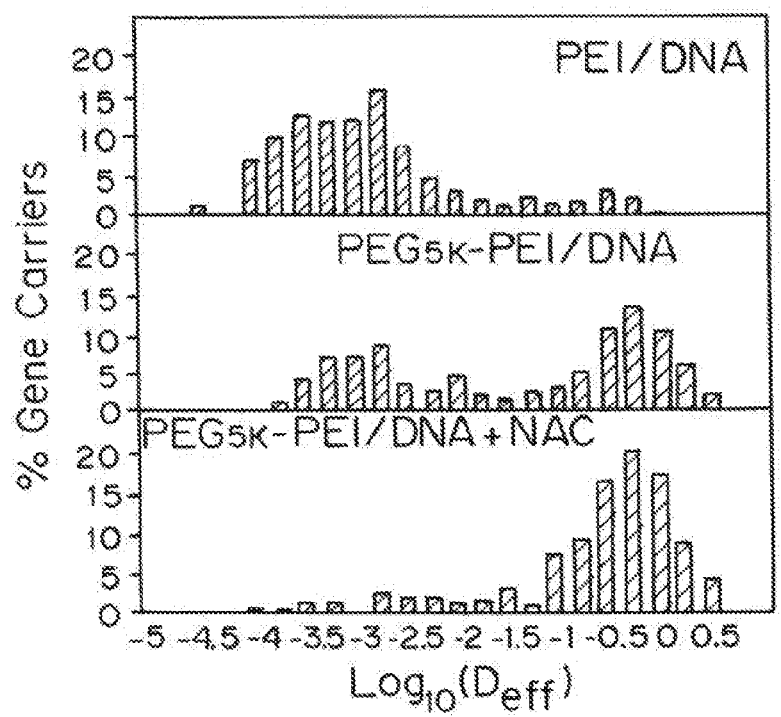
Figure 2D:
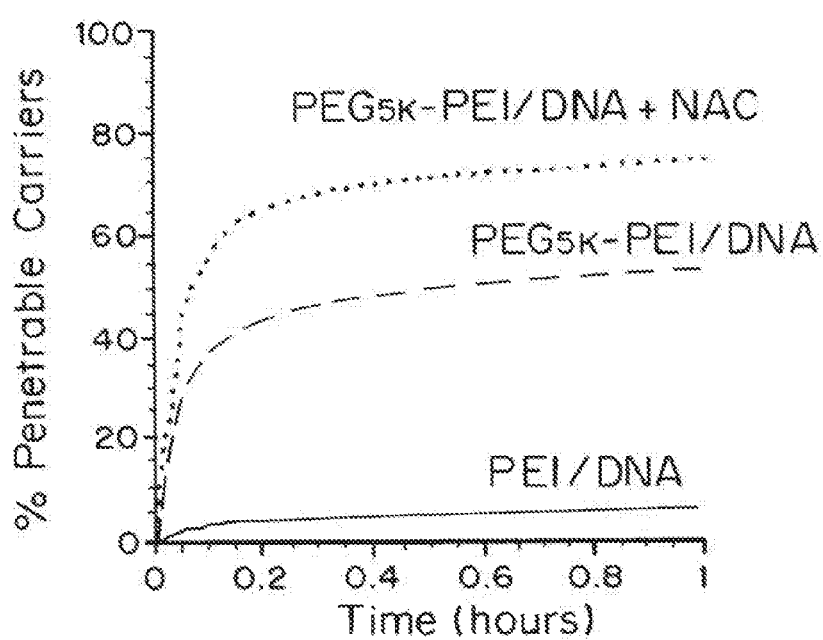

In contrast, PEG$_{5k}$-PEI/DNA displayed trajectories that spanned far greater distances than PEI/DNA (FIG. 2A). The <MSD> of PEG$_{5k}$-PEI/DNA was at least 60-fold greater than that of PEI/DNA (at τ=1 s; FIG. 2B) (p<0.05), with a <$D_{eff}$> in sputum ~100-fold smaller than their theoretical $D_{eff}$ in water (Table 1). The enhanced sputum penetration of PEG$_{5k}$-PEI/DNA is also reflected by the substantially improved α value (α=0.78) compared to PEI/DNA (Table 1). Unlike PEI/DNA, individual $D_{eff}$ distributions for PEG$_{5k}$-PEI/DNA were bimodal, with many trapped gene carriers but also a substantial population that can rapidly penetrate CF sputum (middle panel in FIG. 2C). It can be estimated that roughly 50% of PEG$_{5k}$-PEI/DNA nanoparticle gene earners are capable of diffusing across a 10 μm thick CF sputum layer within 20 min (FIG. 2D and Table 1).

NAC Further Enhances Sputum Penetration by PEG-Coated PEI Gene Carriers.

Despite the improved sputum penetration of PEG$_{5k}$-PEI/DNA due to the PEG coating, there remained a substantial fraction of PEG$_{5k}$-PEI/DNA with very low $D_{eff}$, and the <$D_{eff}$> overall was still much slower than the theoretical speeds in water. NAC treatment increased the <MSD> of PEG$_{5k}$-PEI/DNA by ~3-fold compared to <MSD> in aliquots of the same but untreated sputum samples (p<0.05 for n=4 independent experiments) (τ=1 s; FIG. 2A). Importantly, the <$D_{eff}$> of PEG$_{5k}$-PEI/DNA in NAC-treated sputum corresponds to speeds only ~35-fold slower than their theoretical $D_{eff}$ in water (τ=1 s) (Table 1). The α value for PEG$_{5k}$-PEI/DNA in NAC-treated sputum was 0.87 (Table 1), suggesting that PEG$_{5k}$-PEI/DNA experienced minimal hindrance to Brownian diffusion in NAC-treated sputum. It is worth noting that most of the slow moving PEG$_{5k}$-PEI/DNA found in native sputum (middle panel in FIG. 2C) were eliminated upon NAC treatment (bottom panel in FIG. 2C). Based on the measured $D_{eff}$, it can be estimated that as much as 70% of PEG$_{5k}$-PEI/DNA may penetrate a 10 μm thick NAC-treated sputum layer within 20 min (FIG. 2D and Table 1).

PEG Improves Airway Gene Transfer by PEI-Based Gene Carriers.

Figure 3:
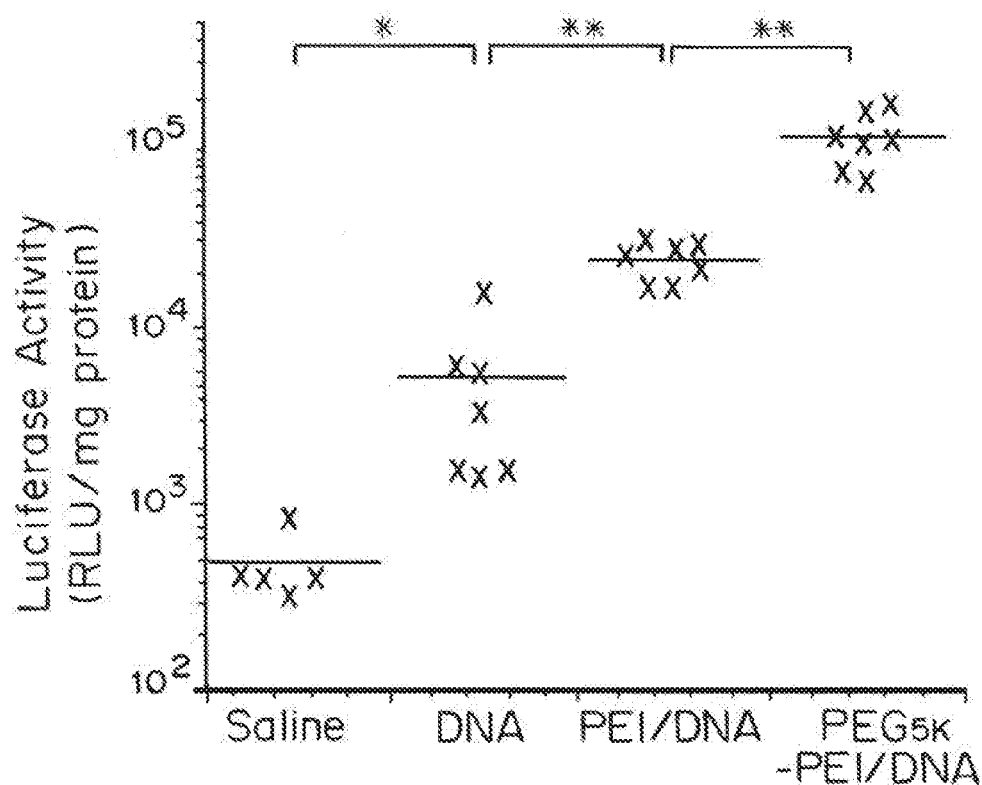
FIG. 3 is a graph plotting the luciferase activity (RLU/mg protein) measured in lung tissue homogenates collected from Balb/c mice 24 hours after intranasal instillation of saline, 50 μg of pd1GL3-RL plasmid DNA, 50 μg pd1GL3-RL plasmid DNA in a PEI/DNA carrier, and 50 ng pd1GL3-RL plasmid DNA in a PEG$_{5k}$-PEI/DNA nanoparticle gene carrier. The average luciferase activity (i.e., gene expression level) mediated by PEI/DNA was ~4-fold higher than that by DNA alone (p<0.001). Inclusion of PEG coatings further enhanced airway gene transfer by ~5-fold compared to PEI/DNA (p<0.001), which corresponds to an average luciferase activity more than 20-fold higher than that of DNA alone (p<0.0005). Overall, the average luciferase activities of DNA alone, PEI/DNA and PEG$_{5k}$-PEI/DNA were 11-, 47-, and ~236-fold higher than that of saline control, respectively.

To test whether improved sputum penetration by nanoparticle gene carriers leads to enhanced airway gene transfer in vivo, mice were intranasally dosed with either luciferase genes alone or compacted with PEI or PEG$_{5k}$-PEI$^{75\%}$ (FIG. 3). The average luciferase activity (i.e., gene expression level) mediated by PEI/DNA was ~4-fold higher than that by DNA alone (p<0.001). Inclusion of PEG coatings further enhanced airway gene transfer by ~5-fold compared to PEI/DNA (p<0.001), which corresponds to an average luciferase activity more than 20-fold higher than that of DNA alone (p<0.0005). Overall, the average luciferase activities of DNA alone, PEI/DNA and PEG$_{5k}$-PEI/DNA were 11-, 47-, and ~236-fold higher than that of saline control, respectively.

To confirm if the enhanced gene transfer mediated by PEG-PEI may be attributed to improved nanoparticle gene carrier diffusion across sputum, the diffusion and distribution of nanoparticle gene carriers in mouse tracheas following the intranasal administration of PEI/DNA and PEG$_{5k}$-PEI/DNA was investigated. A significant fraction of PEG$_{5k}$-PEI/DNA underwent rapid diffusion in the mouse trachea, whereas most of the PEI/DNA were completely immobilized. In good agreement with their mobility, PEG$_{5k}$-PEI/

DNA was widely distributed throughout the lumen of mouse trachea, while PEI/DNA was found only in several confined regions as an aggregate.

The distribution of nanoparticle gene carriers in lung parenchyma 1 hour after the intranasal administration was also examined. $PEG_{5k}$-PEI/DNA was distributed throughout the lung tissue, including most of the airways and alveolar regions, whereas PEI/DNA was sparsely distributed in the lung.

Figure 4A:
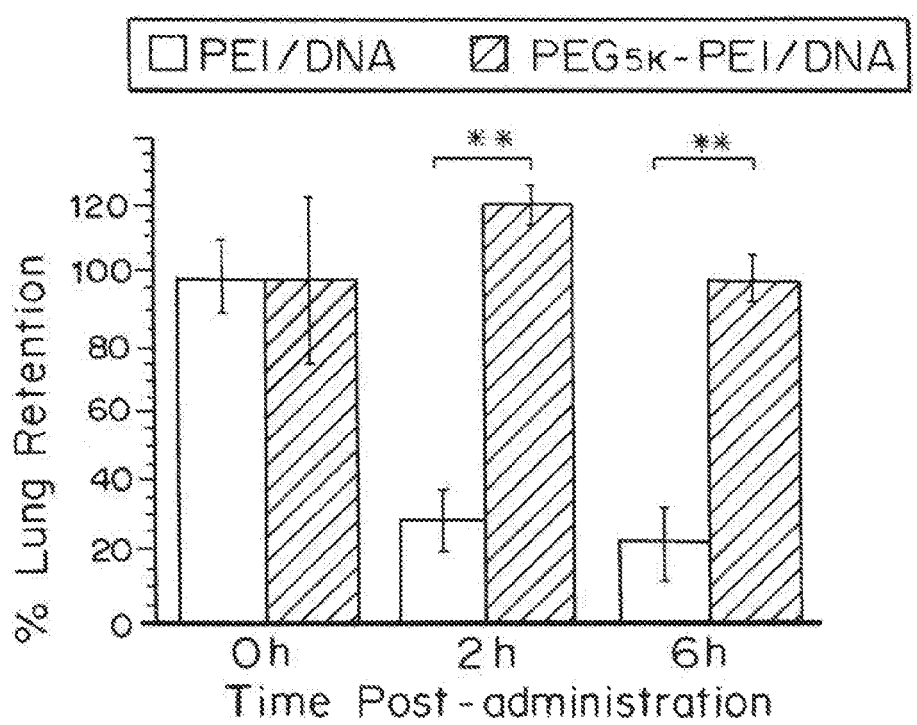
FIGS. 4A-B illustrate the retention and distribution of gene carriers following intranasal instillation in Balb/c mice.
Figure 4B:
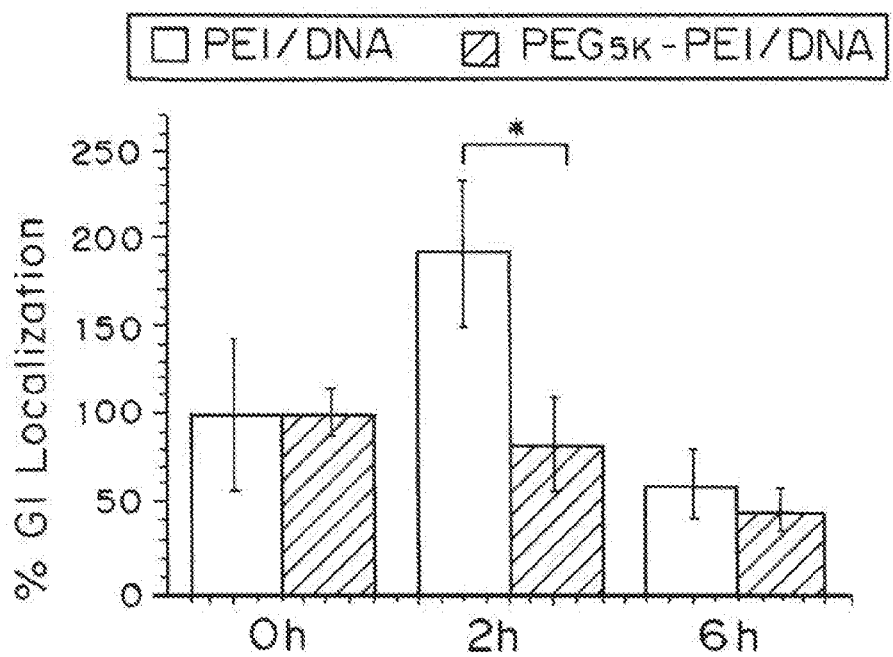

Both PEI/DNA and $PEG_{5k}$-PEI/DNA were distributed in both mouse lungs and upper GI tracts immediately after their intranasal administration. The total fluorescence of $PEG_{5k}$-PEI/DNA was well preserved in mouse lungs up to 6 hours post-administration, whereas that of PEI/DNA was sharply dropped to ~30% of the initial value at 2 hours post-administration, suggesting PEI/DNA was rapidly eliminated from the mouse lungs (FIG. 4A). To investigate whether reduced airway retention of PEI/DNA is attributed to their mucocilliary clearance (MCC), the total fluorescence of nanoparticle gene carriers in the upper GI tracts of the mice was measured. The total fluorescence of PEI/DNA in the upper GI tract was sharply increased at 2 hours post-administration, whereas that of $PEG_{5k}$-PEI/DNA was gradually decreased over time (FIG. 4B).

NAC Moderately Enhance Airway Gene Transfer by PEG-Coated Gene Carriers

Figure 5:
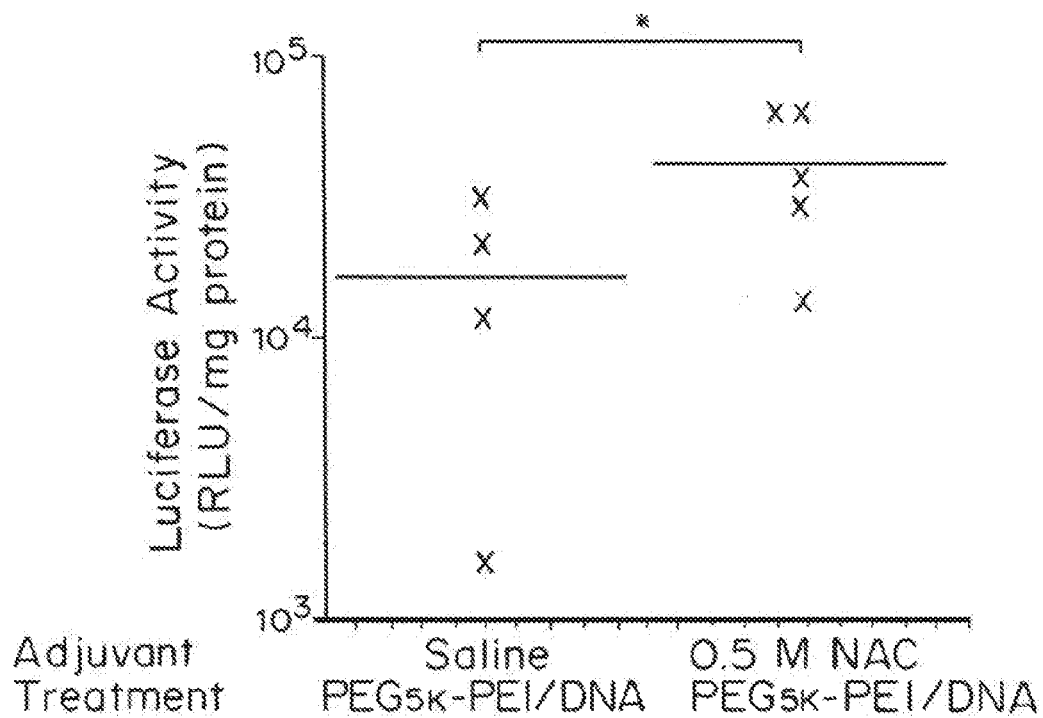
FIG. 5 is a graph plotting the luciferase activity (RLU/mg protein) measured in lung tissue homogenates collected from C57 mice intranasally challenged with *P. aeruginosa* lipopolysaccharide (LPS) 24 hours after intranasal instillation of a 50 μg pd1GL3-RL plasmid DNA in a PEG$_{5k}$-PEI/DNA nanoparticle gene carrier. The right bar shows the average luciferase activity for mice who were pretreated with NAC 30 minutes prior to PEG$_{5k}$-PEI/DNA administration. The left bar shows the average luciferase activity for mice who received a saline control 30 minutes prior to PEG$_{5k}$-PEI/DNA administration. NAC-treated mice exhibited approximately 2-fold higher average luciferase activity compared to the saline-treated counterpart (p<0.05).

The influence of NAC treatment on airway gene transfer mediated by $PEG_{5k}$-PEI/DNA nanoparticle gene carriers was also evaluated (FIG. 5). C57 mice were challenged with *P. aeruginosa* LPS to induce mucus hypersecretion in the mouse airways. The LPS-challenged mice were then treated with either saline or 0.5 M NAC, and finally with nanoparticle gene carriers 30 min later. NAC-treated mice exhibited ~2-fold higher average luciferase activity compared to the saline-treated counterpart ($p<0.05$). However, there was overlap in the gene expression levels in individual mice between the two groups.

PEG Reduced Cytotoxicity and Immune Cell Infiltration Induced by PEI-Based Gene Carriers.

Despite its wide use as gene carrier platform, several groups have reported substantial toxicity for PEI (Beyerle, A. et al. *Toxicol. Appl. Pharmacol.* 242:146-154 (2010), Fischer, D. et al. *Pharm. Res.* 16:1273-1279 (1999), Ogris, M. et al. *Gene Ther.* 6:595-605 (1999)). To address this concern, pulmonary inflammation in the mouse lung following the administration of $PEG_{5k}$-PEI/DNA was evaluated. H & E staining of lung tissue sections suggests PEI/DNA caused an elevated immune cell infiltration compared to saline control. However, no apparent increase in immune cell infiltration as observed in the lungs of mice dosed with $PEG_{5k}$-PEI/DNA compared to saline control, suggesting $PEG_{5k}$-PEI/DNA did hot trigger pulmonary inflammation.

Figure 6:
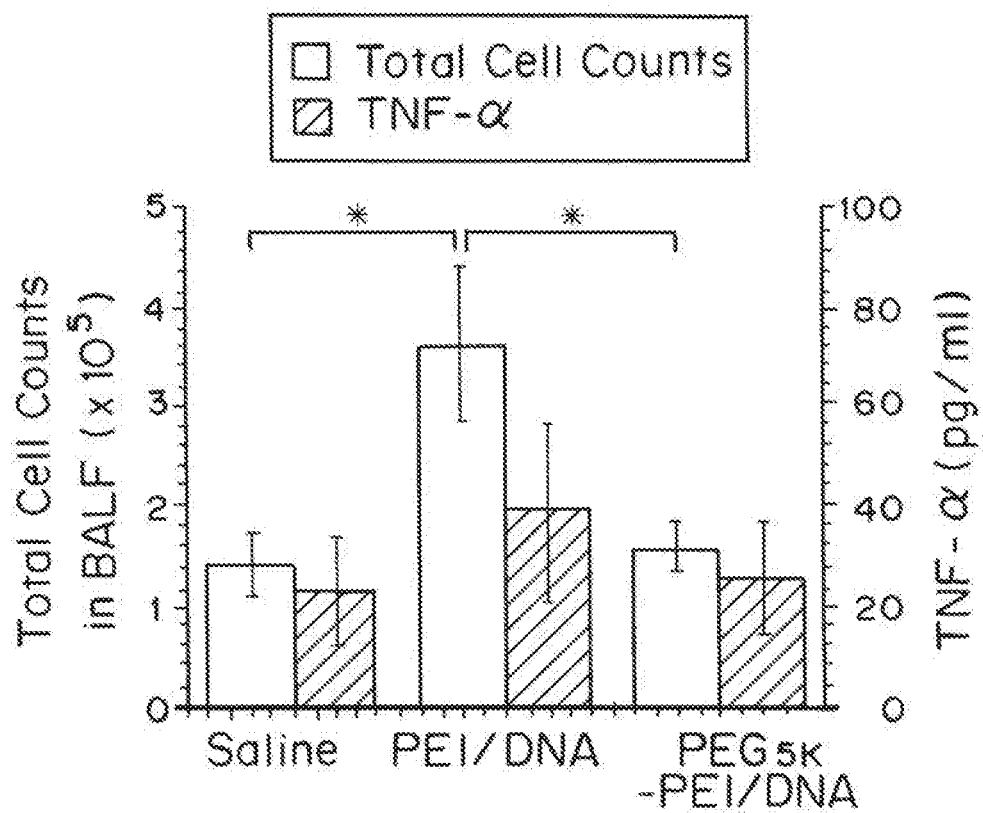
FIG. 6 plots the total cell count (left axis, x 10$^5$, white bars) and the concentration of TNF-α (right axis, pg/ml, gray bars) in bronchioalveolar lavage fluid (BALF) collected from mice intranasally dosed with a saline control, PEI/DNA, and PEG$_{5k}$-PEI/DNA.

The total cell count and the concentration of TNF-α in bronchioalveolar lavage fluid (HALF) from mice intranasally dosed with PEI/DNA and $PEG_{5k}$-PEI/DNA were measured at 24 h post-administration (FIG. 6). Similar to the histological observation, PEI/DNA induced a significant increase in total cell counts ($p<0.05$), a hallmark of pulmonary inflammation (Scheule, R. K. et al. *Hum. Gene Ther.* 8:689-707 (1997)), whereas the total cell counts for $PEG_{5k}$-PEI/DNA was comparable to those for saline control. Differences in the concentration TNF-α in BALF were not statistically significant for all three conditions, suggesting both PEI/DNA and $PEG_{5k}$-PEI/DNA did not induce TNF-α release 24 hours after their administration.

Figure 7A:
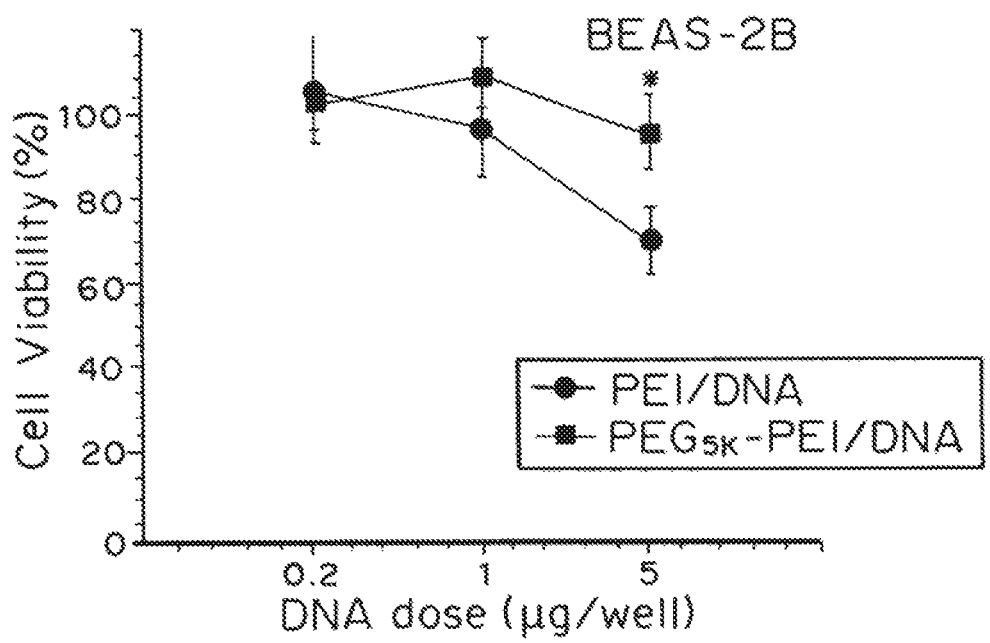
FIGS. 7A-B illustrate the cytotoxicity of PEI/DNA and PEG$_{5k}$-PEI/DNA. The viability of cells was measured after incubating samples of cells for 48 h with varying concentrations of PEI/DNA and PEG$_{5k}$-PEI/DNA gene carriers.
Figure 7B:
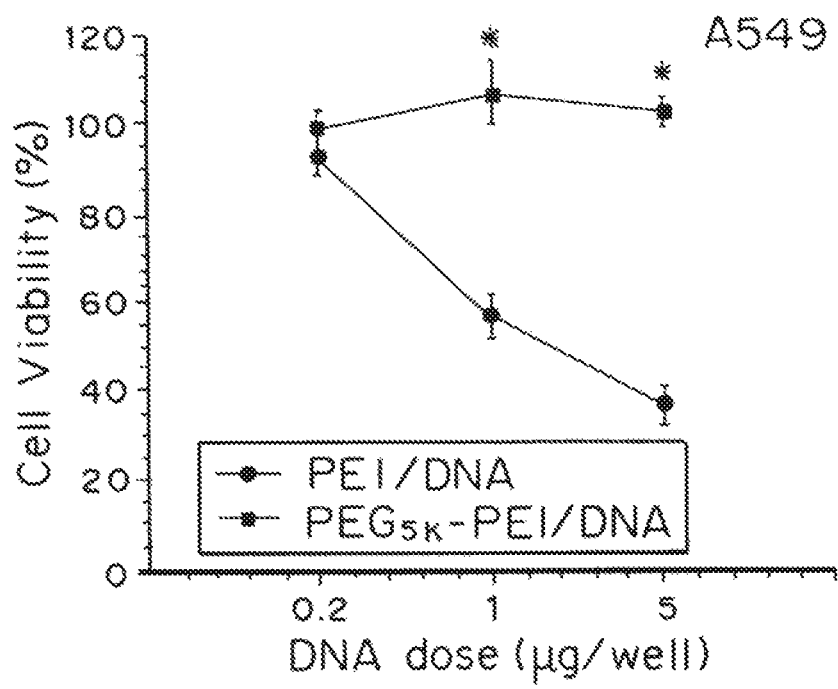

In addition to pulmonary inflammation, the cytotoxicity of nanoparticle gene carriers was evaluated in vitro. Cell viability was determined 48 hours after post-transfection in both human bronchial (FIG. 7A) and alveolar (FIG. 7B) epithelial cell lines. Consistent with the in vivo toxicity study, $PEG_{5k}$-PEI/DNA did not induce cytotoxicity at all doses tested regardless of cell types, whereas PEI/DNA exhibited dose-dependent increase in cytotoxicity in the both cell lines.

Summary

The ability of the nanoparticle gene carriers described herein to rapidly penetrate fresh purulent sputum expectorated by CF patients was demonstrated. The nanoparticle gene carriers protected cargo DNA against enzymatic degradation, remained stable upon long term storage, induced no inflammation or toxicity, and mediated a 5-fold improvement in gene transfer to mice lung compared to PEI/DNA. Without wishing to be bound by theory, the enhanced airway gene transfer observed upon administration of the nanoparticle gene carriers as compared to PEI/DNA is most likely the result to the improved sputum penetration, which leads to a marked increase in the flux of nanoparticle gene carriers that can reach target cells as well as more uniform distribution and prolonged retention in the lung compared to PEI/DNA. This likely results in increased uptake by greater number of cells in the airway epithelium.

CF sputum possess high concentrations of negatively charged macromolecules, including mucins, DNA and actin filaments, which can interact with the cationic PEI necessary to condense plasmid DNA into nanoparticles. To maximize PEG-coating density while still formulating highly compacted nanoparticle gene carriers, 5 kDa PEG was incorporated at high PEG:PEI ratios, and blended in combination with free PEI polymers to prepare nanoparticle gene carriers. The resulting nanoparticle gene carries exhibited high concentrations (density) of PEG on the surface of gene carriers. Indeed, based on the hydrodynamic radius and the N/P ratio necessary to fully compact DNA, the surface PEG density of $PEG_{5k}$-PEI/DNA was estimated to be ~1 $PEG/nm^2$.

Large number of primary amines along the PEI backbone (~40% of ~580 amines in a 25 kDa branched PEI) endows PEI with superior DNA compaction ability, protection of cargo DNA, and buffering capacity. Although PEG conjugation to PEI may allow a dense surface PEG coverage, it requires one-to-one conversion of primary amines to amide bonds, which greatly reduces the positive charge density of PEI at high PEG substitution ratios. Previous studies have shown that increasing the degree of PEG conjugation to PEI led to less efficient DNA compaction and larger particle sizes. This is likely due to fewer positive charges available for compacting DNA as well as steric interference from PEG, and poor DNA compaction may lead to inferior protection of cargo DNA. A high degree of PEG conjugation may also reduce the buffering capacity of the gene carriers and thus the gene transfer efficiency.

By forming nanoparticle gene carriers from a mixture of PEI and PEG-PEI polymers, a nanoparticle with a high surface PEG density was obtained while preserving the efficient compaction and buffering properties of PEI. Nanoparticle gene carriers formed from a mixture of PEI and PEG-PEI polymer were significantly smaller than nanoparticles formed from $PEG_{5k}$-$PEI^{100\%}$/DNA; however, they still possessed a near zero surface charge. This is most likely because more cationic free PEI is localized to the core of $PEG_{5k}$-PEI/DNA, allowing for greater compaction of anionic DNA, while the more neutral $PEG_{5k}$-PEI is localized to the nanoparticle gene earner surface.

PEG$_{5k}$-PEI/DNA exhibited superior DNA protection capacity compared to PEI/DNA, in contrast to a previous finding that gene carriers formulated solely with PEG-PEI at a high PEG:PEI ratio were unable to protect cargo DNA upon enzymatic digestion (Kichler, A. et al. J. Control. Release. 81:379-388 (2002). The inclusion of more than 25% unconjugated PEI led to increased surface charge at all N/P ratios tested, which reflects a substantial decrease in the density of surface-exposed PEG.

Airway inflammation induced by any nanoparticle-based therapeutics may be detrimental to CF patients, since CF airways are already overloaded by bacterial infection and chronic inflammation. Furthermore, cell death induced by cytotoxic effects of therapeutic nanoparticles may cause release of cell debris, which can further thicken CF sputum. PEG$_{5k}$-PEI/DNA did not trigger detectable pulmonary inflammation and cytotoxicity to airway epithelial cells.

NAC further improved the diffusion of PEG$_{5k}$-PEI/DNA in CF sputum. The improved diffusion may be attributed to reduced steric obstruction, since sputum mesh spacings are significantly increased by NAC; in particular, the percentage of small pores (<100 nm), whose sizes are comparable to diameters of PEG$_{5k}$-PEI/DNA, are markedly decreased upon NAC treatment (from over 20% to 5%). Another possibility is that the diffusion of a fraction of PEG$_{5k}$-PEI/DNA, which is not sufficiently coated by PEG, may be improved by reduced adhesion to sputum mesh. The probability of forming multiple adhesive interactions between a nanoparticle gene carrier and the sputum mesh network, necessary for trapping gene carriers in a sputum gel with permanent avidity, is likely reduced by an increase in sputum pore sizes induced by NAC. NAC also improved airway gene transfer of PEG$_{5k}$-PEI/DNA to the lung in mice with induced mucus hypersecretion.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of delivering a nucleic acid across a mucosal surface, the method comprising administering an effective amount of a composition comprising nucleic acid nanoparticles, the nucleic acid nanoparticles comprising:
    a) a complex formed by the ionic association of one or more nucleic acids and one or more polycationic polymers, and
    b) one or more mucus-resistant/diffusive graft co-polymers non-covalently associated to the complex, wherein the nucleic acid nanoparticles have an average diameter of between 5 and 500 nm,
    wherein the one or more mucus-resistant/diffusive graft co-polymers comprise a polycationic polymer backbone having multiple mucus-resistant/diffusive polymer side chains covalently attached thereto,
    wherein the ratio of mucus-resistant/diffusive polymer side chains to the polycationic backbone is between 15:1 and 60:1, or wherein the one or more polycationic polymers and one or more mucus-resistant/diffusive graft co-polymers are present in a molar ratio of between 1:5 and 5:1; and
    wherein the nanoparticles have a near neutral surface charge between about −10 mV and about +10 mV.

2. The method of claim 1, wherein the nanoparticles are 300 nm or smaller.

3. The method of claim 1, wherein the one or more mucus-resistant/diffusive polymers are polyalkylene oxide polymers or copolymers.

4. The method of claim 3, wherein the polyalkylene oxide polymer is polyethylene glycol.

5. The method of claim 4, wherein the polylalkylene oxide polymer comprises polyethylene oxide-polypropylene oxide block copolymers.

6. The method of claim 1, wherein the one or more mucus-resistant/diffusive polymers have a molecular weight of between about 500 to 10,000 Daltons.

7. The method of claim 6, wherein the one or more mucus-resistant/diffusive polymers have a molecular weight of between about 2,000 to 7,500 Daltons.

8. The method of claim 1, wherein the polycationic polymer is selected from the group consisting of polyethyleneimine (PEI), polyarginine, polylysine, polyhistidine, and copolymers thereof.

9. The method of claim 1, wherein the polycationic polymer has a molecular weight between 5000 and 50,000.

10. The method of claim 1, wherein the polycationic polymer is conjugated to one or more mucus-resistant/diffusive polymers.

11. The method of claim 10, wherein the mucus-resistant/diffusive polymer is a graft copolymer, having a polycationic backbone having multiple mucus-resistant/diffusive polymer side chains covalently attached thereto, wherein the ratio of mucus-resistant/diffusive polymer side chains to the polycationic backbone is between 20:1 and 70:1.

12. The method of claim 1, wherein the nucleic acid is selected from the group consisting of DNA, RNA, stabilized nucleic acid encoding proteins, nucleic acid molecules complementary to the gene or nucleic acid molecule encoding proteins, and nucleic acid molecules correcting defects in the gene.

13. The method of claim 1, wherein the mucosal surface is a pulmonary, ocular, nasal, buccal, vaginal, gastrointestinal, or rectal mucosal surface.

* * * * *

UNITED STATES PATENT AND TRADEMARK OFFICE
CERTIFICATE OF CORRECTION

| | | |
|---|---|---|
| PATENT NO. | : 9,675,711 B2 | Page 1 of 1 |
| APPLICATION NO. | : 15/144077 | |
| DATED | : June 13, 2017 | |
| INVENTOR(S) | : Jung Soo Suk and Justin Scot Hanes | |

It is certified that error appears in the above-identified patent and that said Letters Patent is hereby corrected as shown below:

In the Specification

Column 1, Lines 20-24 (government support statement) please replace the following:
STATEMENT OF GOVERNMENTAL INTEREST
This invention was made with government support under grant numbers HL051811, EB003558, awarded by the National Institutes of Health. The government has certain rights in the invention.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*